(12) United States Patent
Aragón Reyes et al.

(10) Patent No.: US 9,529,000 B2
(45) Date of Patent: Dec. 27, 2016

(54) NON-INVASIVE DIAGNOSTIC METHOD FOR THE EVALUATION OF INTESTINAL LACTASE DEFICIENCY (HYPOLACTASIA)

(71) Applicant: VENTER PHARMA, S.L., Alcobendas (ES)

(72) Inventors: Juan José Aragón Reyes, Alcobendas (ES); Alfonso Fernandez-Mayoralas Alvarez, Alcobendas (ES); Carmen Hermida Diaz, Alcobendas (ES)

(73) Assignee: VENTER PHARMA, S.L., Madrid (ES)

( * ) Notice: Subject to any disclaimer, the term of this patent is extended or adjusted under 35 U.S.C. 154(b) by 6 days.

(21) Appl. No.: 14/819,028

(22) Filed: Aug. 5, 2015

(65) Prior Publication Data
US 2015/0338421 A1 Nov. 26, 2015

Related U.S. Application Data

(62) Division of application No. 13/350,097, filed on Jan. 13, 2012, now Pat. No. 9,128,100.

(60) Provisional application No. 61/433,002, filed on Jan. 14, 2011.

(51) Int. Cl.
*G01N 33/68* (2006.01)

(52) U.S. Cl.
CPC ..... *G01N 33/6893* (2013.01); *G01N 2333/924* (2013.01); *G01N 2800/02* (2013.01); *G01N 2800/06* (2013.01)

(58) Field of Classification Search
None
See application file for complete search history.

(56) References Cited

U.S. PATENT DOCUMENTS

| | | | |
|---|---|---|---|
| 5,994,092 A | 11/1999 | Aragon Reyes et al. | |
| 7,537,909 B2 | 5/2009 | Vicinay et al. | |
| 9,128,100 B2 | 9/2015 | Aragon Reyes et al. | |
| 2005/0238580 A1 | 10/2005 | Aragon Reyes et al. | |

FOREIGN PATENT DOCUMENTS

| | | |
|---|---|---|
| ES | 478590 A1 | 3/1979 |
| ES | 482073 A2 | 6/1979 |
| ES | 2023556 | 6/1990 |
| ES | 2100131 B1 | 11/1995 |
| ES | 2182703 B1 | 6/2001 |
| ES | 2208099 B1 | 10/2002 |
| WO | 9717464 A1 | 5/1997 |
| WO | 02103038 A1 | 12/2002 |
| WO | 2004035814 A1 | 4/2004 |

OTHER PUBLICATIONS

H. Arola, "Diagnosis of Hypolactasia and Lactose Malabsorption," Scand J. Gastroenterol, 1994, pp. 26-35, vol. 29, s202.
Davidson, Geoffrey P., et al; "Value of Breath Hydrogen Analysis in Management of Diarrheal illness in Childhood: Comparison with Duodenal Biopsy," Journal of Pediatric Gastroenterology and Nutrition, 1985, pp. 381-387, vol. 4.
Dawson, DJ, "Lactose digestion by human jejunal biopsies: the relationship between hydrolysis and absorption," Gut, 1986, pp. 521-527, vol. 27.
Koetse, H.A., et al; "Non-Invasive Detection of Low-Intestinal Lactase Activity in Children by Use of a Combined 13CO2/H2 Breath Test," Scandinavian Journal of Gastroenterology, 1999, pp. 35-40, vol. 34.
Levitt, Michael D., "Production and Excretion of Hydrogen Gas in Man," The New England Journal of Medicine, 1969, pp. 122-127, vol. 281.
Lifschitz, Carlos H., et al.; "Absorption and Tolerance of Lactose in Infants Recovering from Severe Diarrhea," Journal of Pediatric Gastroenterology and Nutrition, 1985, pp. 942-948, vol. 4.
McGill, Douglas B., et al.; "Comparison of Venous and Capillary Blood Samples in Lactose Tolerance Testing," Gastroenterology, 1967, pp. 371-374, vol. 53.
Metz, Geoffrey, et al.; "Breath Hydrogen as a Diagnostic Method for Hypolactasia," The Lancet, 1975, pp. 1155-1157.
Newcomer, Albert D., et al.; "Distribution of Disaccharidase Activity in the Small Bowel of Normal and Lactase-Deficient Subjects," Gastroenterology, 1966, pp. 481-488, vol. 51.
Newcomer, Albert D., et al.; "Prospective Comparison of Indirect Methods for Detecting Lactase Deficiency," The New England Journal of Medicine, 1975, pp. 1232-1236—vol. 293.
Sasaki, Yasuhito, et al.; "Measurement of C-lactose absorption in the diagnosis of lactase deficiency," Journal of Lab Clinical Medicine, 1970, pp. 824-835, vol. 76.
Semenza, Giorgio, et al.; "Small-Intestinal Disaccharidases," The Metabolic and Molecular Bases of Inherited Disease, 2001, pp. 1621-1650, 8th Edition.
Triadou, N., et al.; "Longitudinal Study of the Human Intestinal Brush Border Membrane Proteins," Gastroenterology, 1983, pp. 1326-1332, vol. 85.
Hermida et al., "Noninvasive evaluation of intestinal lactase with 4-Galactoslyxylose: comparison with 3- and 2-Galactosylxylose and optimization of the method in rats", Clinical Chemistry, 2006, pp. 270-277, vol. 52.

*Primary Examiner* — Anand Desai
(74) *Attorney, Agent, or Firm* — Tristan A. Fuierer; Moore & Van Allen, PLLC

(57) ABSTRACT

The test of the invention comprises the measuring the total amount of xylose in urine and/or its concentration in blood following oral administration of 4-O$\beta$-D-galactopyranosyl-D-xylose (4-GX) to the patient. It is a non-invasive test that is based on the direct evaluation of the global enzyme activity in the whole individual, not on measuring the metabolic consequences derived from its deficiency. It does not require specialised equipment, does not cause apparent discomfort in patients with lactase deficiency and is very reliable, thus overcoming the drawbacks of the diagnostic tests currently in use and is a statistically significantly better test in terms of its reliability; consequently it should become the reference or gold standard test for the indication of hypolactasia.

8 Claims, 7 Drawing Sheets

E

F

NON-INVASIVE DIAGNOSTIC METHOD FOR THE EVALUATION OF INTESTINAL LACTASE DEFICIENCY (HYPOLACTASIA)

CROSS REFERENCE TO RELATED APPLICATIONS

This application is filed under the provisions of 35 U.S.C. §111(a) and is a divisional of U.S. patent application Ser. No. 13/350,097 filed on Jan. 13, 2012, and entitled "Non-Invasive Diagnostic Method for the Evaluation of Intestinal Lactase Deficiency (Hypolactasia)" in the name of Juan José ARAGÓN REYES et al., which claims the benefit of U.S. Provisional Patent Application No. 61/433,002 filed on Jan. 14, 2011, both of which are hereby incorporated by reference herein in their entirety.

TECHNICAL FIELD OF THE INVENTION

The invention is included in the pharmaceutical sector and is applicable in the medical diagnostic sector for the evaluation of intestinal lactase activity, specifically in intestinal lactase deficiency (hypolactasia) in humans as a non-invasive test of the activity of this enzyme.

STATE OF THE ART

Intestinal lactase is the enzyme responsible for lactose digestion. Lactase is located in the microvilli, which constitute the so-called brush border of the enterocytes of the small intestine, it is an integral protein of the cell membrane with its active centre directed towards the lumen of the small intestine, and its activity varies along the length of the intestine, the highest activity being found in the middle jejunum (Newcomer, A. D. et al., 1966; Gastroenterology 51, 481-88; Triadou, N. et al., 1983; Gastroenterology 85, 1326-32). Lactose is not absorbed like other disaccharides through the intestinal mucosa but must be hydrolysed by lactase into its components of galactose and glucose, which are then absorbed, this enzyme accounting for all intestinal lactase activity (Semenza, G. et al., 2001. The Metabolic and Molecular Bases of Inherited Disease. McGraw-Hill. Vol I, pp 1623-1650). The hydrolysis of this disaccharide is the rate limiting step in the digestion and use of lactose (Dawson, D. J. et al., 1986; Gut 27, 521-27).

If there is a lack of lactase, lactose is not hydrolysed in the small intestine inducing a reduction in gastric emptying speed, increase in intestinal transit time, increase in osmotic pressure and retention of fluid in the intestinal cavity, giving rise to bacterial fermentation of this fluid in the colon and to the production of gasses such as hydrogen, methane and carbon dioxide and to the formation of short chain fatty acids. As a consequence of these effects, the digestion process is reduced and absorption of monosaccharides falls, giving rise to pain and abdominal cramps, flatulence, audible intestinal noise and diarrhoea. In the adult, this set of symptoms is known as hypolactasia or lactose intolerance and is a very common genetic disorder, affecting to more than a half of the human species. In the newborn, congenital deficiency of the enzyme prevents proper utilisation of lactose resulting in severe disorders such as intense diarrhoea and dehydration, derived both from the reduction of energy input and the intestinal accumulation of non-hydrolysed disaccharide, which requires early detection and a change in diet to lactose-free milk. Lactase deficiency also occurs in a secondary way in a significant number of intestinal pathologies that are accompanied by various degrees of degradation of the intestinal mucosa including celiac disease, inflammatory chronic intestinal disease (Crohn's disease and ulcerative colitis), irritable bowel syndrome, intestinal resection, cystic fibrosis, premature infants, chemotherapy treatments or as an additional disorder of old age. The evaluation of lactase activity is therefore of particular interest in gastroenterology, paediatrics and generally in pathological processes where functional integrity of intestinal mucosa or a differential diagnosis with the deficiency of this enzyme must be assessed.

Two classes of methodologies are used for the diagnosis of intestinal lactase deficiency or lactose intolerance, which have a series of disadvantages that in general imply poor reliability and serious discomfort for patients and also require specialised equipment:

Direct determination of lactase activity in a sample of intestinal mucosa obtained by biopsy using endoscopy (Newcomer, A. D. et al., 1966; Gastroenterology 51, 481-88, Semenza, G. et al, 2001. The Metabolic and Molecular Bases of Inherited Disease. McGraw-Hill. Vol I, pp 1623-1650; Arola, H., 1994; Scand. J. Gastroenterol. 202 (29Suppl), 22-35). This is an invasive method, which only indicates enzyme activity in a specific part or area of the intestine, which is generally not the area of highest occurrence of the enzyme (middle jejunum), as it is very difficult to take biopsies in this area. The result varies from one sample to another, therefore does not provide information about the total enzyme activity in an individual. A poor correlation has been observed between clinical symptoms of lactose intolerance and lactase activity measured in intestinal mucosa.

Indirect determination, evaluating the metabolic consequences of enzyme deficiency after the oral lactose overload test (administration of 1-2 g of lactose per kg body weight to a maximum of 50 g) such as the appearance of symptoms in the subject (abdominal pain, flatulence, diarrhoea, etc.), the determination either in blood or urine of glucose or galactose levels (McGill, D. B. et al., 1967; Gastroenterology 53, 371-74; Newcomer, A. D. et al., 1975; N. Engl. J. Med. 293, 1232-36), determination of the products of lactose hydrolysis by lactase, either by measurement of gases in the breath such as, for example, $H_2$ (Arola, H., 1994. Scand. J. Gastroenterol. 202 (29Suppl), 22-35; Newcomer, A. D. et al., 1975; N. Engl. J. Med. 293, 1232-36; Levitt, M. D., 1969; N. Engl. J. Med. 281, 122-27; Metz, G. et al., 1975; Lancet 1, 1155-57) or exhaled $CO_2$ (Newcomer, A. D. et al., 1975; N. Engl. J. Med. 293, 1232-36; Koetse, H. A. et al., 1999; Test. Scand. J. Gastroenterol. 34, 35-40; Sasaki, Y. et al., 1970; J. Lab. Clin. Med. 76, 824-35). The main problems with these types of indirect test derive from the significant degree of accompanying digestive discomfort, as it is necessary to administer an oral overload of lactose in order to carry them out, this being particularly severe in infants. Also, as these are indirect tests, they do not enable the evaluation of total enzyme activity in an individual but depend on endogenous production capacity of gases such as $H_2$ and $CO_2$ by the subject. In addition to being variable from one individual to another, this is affected by various factors beyond the quantity or activity of lactase enzyme such as smoking habit, type of diet and prior exercise, emotional state, diabetes, use of antibiotics, etc.; so there is a high proportion of false positives and false negatives resulting in poor test reliability. Various studies have demonstrated poor correlation between clinical symptoms of lactose intolerance and the data provided by these types of tests (Davidson, G. P. et al., 1985; J. Pediatr. Gastroenterol. Nutr. 4, 381-87; Lifshitz, C. H. et al., 1985; J. Pediatr. Gastroenterol. Nutr. 4, 942-94845, 46).

In summary, indirect methods, although non-invasive, suffer from three fundamental problems:
i) serious accompanying discomfort to patients with lactase deficiency due to the high lactose doses that must be ingested in all cases;
ii) need for special and unusual equipment and which is not always available in all health centres;
iii) relative frequency of false positives and false negatives.

These drawbacks result in diagnoses of lactase deficiency being made much less frequently than the high level of incidence in the population would lead one to expect.

For these reasons, new diagnostic methods involving little discomfort, simplicity of application and greater reliability are being developed. These are methods for the evaluation of intestinal lactase activity based on the use of specific disaccharides, structural analogues of lactose, and which can function as substrates for the enzyme, and which once ingested, are transformed by the action of intestinal lactase into certain monosaccharides that are absorbed by intestinal mucosa and can be determined in the blood or urine.

Spanish patents ES478590 and ES482073 disclose methods based on the evaluation of intestinal lactase activity by oral administration of 3-O-methyl lactose, a structural analogue of lactose, and the determination of 3-O-methyl-D-glucose in the urine. But these types of analogues have not been used in clinical practice as they imply the absorption into the bloodstream of a non-physiological compound, such as 3-O-methyl-D-glucose, and require gas chromatography or high pressure liquid chromatography systems for the determination.

Spanish patent ES 2023556 discloses the preparation of the disaccharide, 4-O-β-galactopyranosyl-D-xylose (4-GX), for the evaluation of intestinal lactase activity. This disaccharide is administered orally and acts as a substrate of intestinal lactase, being hydrolysed in the intestinal tract into xylose and galactose. Both compounds are absorbed and a substantial part of xylose is eliminated in the urine where it can be directly determined by a simple colorimetric method. The quantity of xylose excreted in the urine is correlated with the levels of intestinal lactase.

Spanish patent ES 2100131 describes enzymatic processes for the preparation of mixtures of galactopyranosyl-xylose disaccharides containing 4-GX and its regioisomers, 2-O-β-galactopyranosyl-D-xylose and 3-O-β-galactopyranosyl-D-xylose, and the use of a mixture of these three regioisomers in the evaluation of intestinal lactase activity in suckling rats of 12 to 30 days of age. A dose of 16.2 mg of the above-mentioned mixture was administered and urine was collected for the next 5 hours, determining therein the eliminated xylose by colorimetric analysis based on reaction with phloroglucinol and using basal urine as the blank. A group of these animals was later sacrificed and the lactase activity in the intestinal mucosa was determined directly. The experiment was repeated in the other animals at days 15, 18, 21, 24 and 30. This specification demonstrated that the elimination of xylose in the urine after oral administration of the mixture to animals during their development phase was proportional to intestinal lactase activity determined post-mortem in the intestinal mucosa of these same animals.

Similarly, Spanish patent ES 2182703 discloses an enzymatic process for obtaining 4-GX that involves an enzymatic reaction between D-xylose and a substrate, B-D-xylopyranoside, and a subsequent phase of isolation and purification of 4-GX. The use of 4-GX in the preparation of compositions and solutions that are useful for the evaluation of intestinal lactase in humans is also described.

4-GX functions as a structural analogue of lactose, the physiological substrate of lactase, so that after its oral administration it is hydrolysed by the intestinal mucosa enzyme, passing the reaction products into the blood, and one of them, xylose, also appears in the urine. In said biological fluid, its concentration can be evaluated by a simple colorimetric determination based on reaction with phloroglucinol. Compared with the methods used in the state of the art for the diagnosis of intestinal lactase deficiency, this method has the following advantages:

High reliability, as this method is based on the direct evaluation of enzyme activity through the determination of xylose in urine or blood (plasma), not on the evaluation of metabolic consequences deriving from its deficiency. The information provided is indicative of total lactase activity in the individual.

High sensitivity: the lower detection limit of xylose when determined by colorimetric analysis based on reaction with phloroglucinol is 0.1 µg.

Simplicity of the required equipment, routinely available in any heath centre with minimal clinical biochemistry laboratory facilities, as the evaluation of the enzyme level is only based on xylose determination, which can be performed by a simple colorimetric test. Furthermore, this technique does not require training or development of new analysis methods as xylose determination is a routine analytical technique in the clinic.

Avoidance of discomfort or adverse gastrointestinal effect in patients with lactase deficiency while carrying out the test. The oral dose of 4-GX administered is very low, since the sensitivity of xylose determination is very high. It should also be pointed out that the hydrolysis of 4-GX by intestinal lactase results in the appearance of two physiological products, galactose and xylose, which are eventually absorbed by the intestinal mucosa. The method does not demand active participation by the subject, so is of particular interest in infants. There is no need to administer compounds labelled with radioactive isotopes.

These studies performed with 4-GX for the evaluation of intestinal lactase demonstrate that this is a harmless, rapid and very simple test that requires minimal equipment and can be highly reliable as it depends directly on the total lactase activity of the individual. Therefore the object of the present invention is to define the optimum doses and times for the evaluation of intestinal lactase activity in humans using non-invasive processes by the oral administration of a structural analogue of lactose, 4-GX, with this test having the potential to become the reference or gold standard test for the determination of intestinal lactase deficiency.

Spanish patent ES 2208099 discloses the use of 4-GX in humans for the evaluation of intestinal lactase as a non-invasive diagnostic test for the deficiency of this enzyme. This patent demonstrates that the excretion of xylose in urine of healthy lactose-tolerant adult volunteers over a period of 8 hours following the administration of the disaccharide increased with the quantity of 4-GX ingested when this was administered at doses of 0.25, 0.5, 1.0 and 3.0 g. This demonstrates that the elimination of xylose by human subjects is dependent on the dose of 4-GX administered, with a dose of 0.25 g of 4-GX being sufficient to enable reliable detection of xylose in urine after the ingestion of the compound. The administration of this dose of 4-GX to adult volunteers with lactose intolerance, who have intestinal lactase deficiency, gives rise to a marked reduction in the elimination of xylose in urine compared to the average values observed in lactose-tolerant volunteers, and depended on the degree of enzyme deficiency. This demonstrates that the method presented in the patent enables the evaluation of intestinal lactase activity and is a valid test for non-invasive diagnosis of the deficiency of this enzyme in humans. This same patent showed that oral administration of 3 g of 4-GX to lactose-tolerant adult volunteers gave rise to the gradual appearance of xylose in blood plasma samples of these volunteers, determined colorimetrically with phloroglucinol. The gradual appearance of xylose in plasma reached a maximum around 2 hours after the ingestion of the disaccharide. Oral administration of the same quantity of 4-GX to a lactose-intolerant adult volunteer diagnosed as hypolactasic resulted in a markedly reduced amount of xylose determined in blood plasma in this subject at 2 hours following ingestion of the disaccharide. This patent therefore demonstrates that the determination of xylose in blood following oral administration of 4-GX enables the evaluation of intestinal lactase activity and may also be a valid test for non-invasive diagnosis of the deficiency of this enzyme in humans. The above mentioned patent therefore concludes that, taking into account the pattern of xylose appearance in blood and urine with time following oral administration of 4-GX to lactose-tolerant and lactose-intolerant volunteers and the high sensitivity of the method used for colorimetric evaluation of xylose with phloroglucinol, the samples of body fluids to be used with this method in adult subjects can be basal urine prior to ingestion of 4-GX and total urine collected for 3 or 4 hours after ingestion of this compound, or a basal blood sample prior to ingestion of 4-GX and another blood sample extracted 2 hours after the administration of that compound.

However, one of the remaining problems in the state of the art is to determine the reference values beyond which a subject analysed could be considered to present lactose intolerance. The test disclosed in ES 2208099 also shows long analysis times of over 2 hours, which would be excessive for patients, including babies, who have been fasting for at least 8 hours before performing the test. Moreover, this time are also excessive for processing a high number of samples.

In this sense, the present invention describes the doses and times used for the evaluation of intestinal lactase activity in humans by non-invasive processes through the oral administration of a structural analogue of lactose, 4-GX, with the determination of normal limits or cut-off points obtained for the concentration of xylose in blood and urine. Lower values of xylose compared to the normal limits described in the present invention are considered as positive, i.e. as indicative of intestinal lactase deficiency, the cause of clinical symptoms of lactose intolerance. This patent concludes that the optimum dose of 4-GX to be administered to correctly diagnose (the term correctly diagnose being understood to mean performing a diagnostic test in which subjects deficient in intestinal lactase are distinguished from normal subjects with high reliability) of the degree of hypolactasia is 0.5 g and the time required for urine collection is not less than 4 hours and not greater than 5 hours in order to ensure a sufficient quantity of excreted xylose. The lowest does of 4-GX to be administered to correctly diagnose the degree of hypolactasia using xylose concentration in plasma is 3 g, with the sample of plasma to be obtained 90 minutes after the oral administration of the disaccharide. In patent ES 2208099, the measurement sample was taken at 120 minutes following administration of 4-GX, the present invention thus demonstrating surprisingly that the optimum time for sampling is approximately 25% shorter, which additionally enables more determinations or diagnostic tests to be carried out using the method described in the present invention, more importantly with higher levels of reliability.

The doses of 4-GX to be administered, the times for measuring the concentration of xylose both in blood and urine samples and the determination of the normal ranges obtained in healthy volunteers for the diagnosis of intestinal lactase deficiency by the administration of various doses of 4-GX make this a new "gold standard" test for the diagnosis of intestinal lactase activity by non-invasive methods, which did not exist to date. The reference or gold standard test until the present invention was taken to be the biopsy test, which, as previously described, is an invasive test and only indicates the activity of the enzyme in a particular part of the intestine from which the biopsy is taken, which additionally does not usually coincide with the area of maximum enzyme levels.

As can be seen in the present invention, no clinically significant adverse reactions were found at any of the doses of 4-GX used, all of them showing a similar safety and tolerance profile.

DESCRIPTION OF THE INVENTION

Brief Description of the Invention

The present invention describes the sensitivity, specificity, positive predictive value and negative predictive value of the non-invasive test of the activity of intestinal lactase based on oral administration of 4-GX and the subsequent determination in urine and/or blood of its hydrolysis product, xylose.

One of the main objectives of the present invention has been to establish the lower limits of xylose concentration in healthy individuals using the tests with 4-GX on blood and/or urine described in the invention. Thus individuals presenting lower values of xylose compared to the normal limits described in the present invention are considered as individuals with intestinal lactase deficiency, the cause of clinical symptoms of lactose intolerance. The results obtained using the doses and times described in the present invention are compared with those obtained by tests used in clinical practice to date: samples of intestinal biopsy, hydrogen breath test and the capillary-blood glucose test.

By means of the statistical data shown in the present invention regarding the optimum doses and times used for the tests described in the present invention compared to data obtained by the other tests performed and that are part of the state of the art, it is concluded that the test of measuring intestinal lactase activity by the administration of 4-GX, described in the present invention, be considered to be the reference or gold standard test for the diagnosis of hypolactasia, since in addition to being a non-invasive test it is capable of distinguishing false positives and false negatives that appear in the tests performed using the older reference method: measurement of intestinal lactase in biopsy, taking as a comparison the normal limit used in clinical practice for this diagnostic test. These characteristics, along with the absence of adverse reactions in intolerant patients and the simplicity of carrying out the test, make the tests described in the present invention into an optimum functional diagnostic for the diagnosis of lactose intolerance.

Obtaining the above mentioned statistical data on sensitivity, specificity, positive predictive value and negative predictive value were carried out following the administration of a single oral dose of 3 g of 4-GX for the determination of the maximum concentration of xylose in plasma and 0.5 g of 4-GX for the determination of the total amount of xylose excreted in urine. The concentration of xylose in the blood (plasma) was measured 90 minutes after ingestion of 4-GX and the amount of xylose in urine was measured in the total urine collected for up to 4 hours following the administration of the above indicated dose of 4-GX (0-4-hour urine) and/or in the total urine collected up to 5 hours after the administration of the above indicated dose of 4-GX (0-5-hour urine).

For the effects of the present invention, the term gold standard test or reference test is a diagnostic test that is considered to be definitive for diagnosing a disease in an individual; in the case of the present invention, the non-invasive test for the diagnosis of intestinal lactase deficiency with 4-GX under the conditions described (administered amounts and times of measurement) is considered to be the gold standard test or reference test for the diagnosis of hypolactasia, using either plasma or urine.

For the effects of the present specification, the terms: reference threshold value, normal limit, lower limit of normal, cut-off point and cut-off are synonymous, all of them being defined as those values below which a patient is diagnosed as hypolactasic by the 4-GX test described in the present invention.

DETAILED DESCRIPTION OF THE INVENTION

Figure 1:
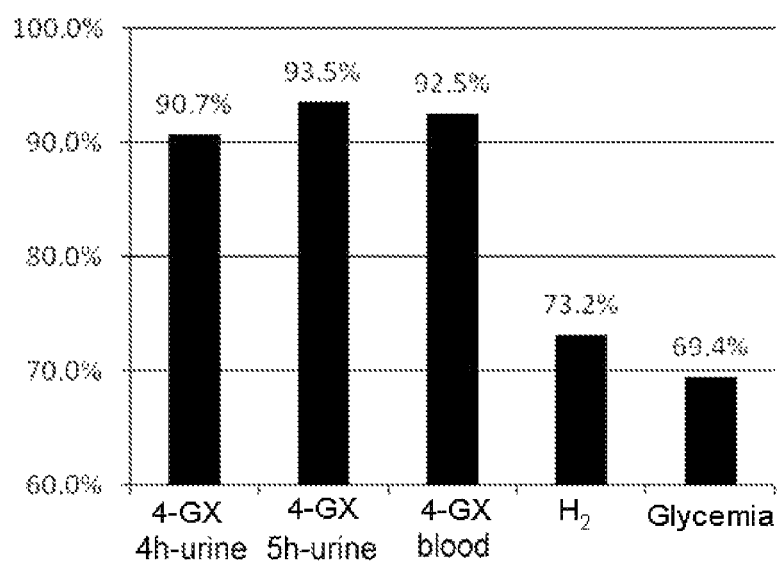
FIG. 1. Percentages of sensitivity (A), specificity (B), positive predictive value (C), negative predictive value (D), positive likelihood ratio (E) and negative likelihood ratio (F) of the various tests performed in patients (n=205) with symptoms suggestive of lactose intolerance after the administration of different doses of 4-GX compared to the determination of intestinal lactase activity in biopsy taken as the gold standard test.
Figure 1:
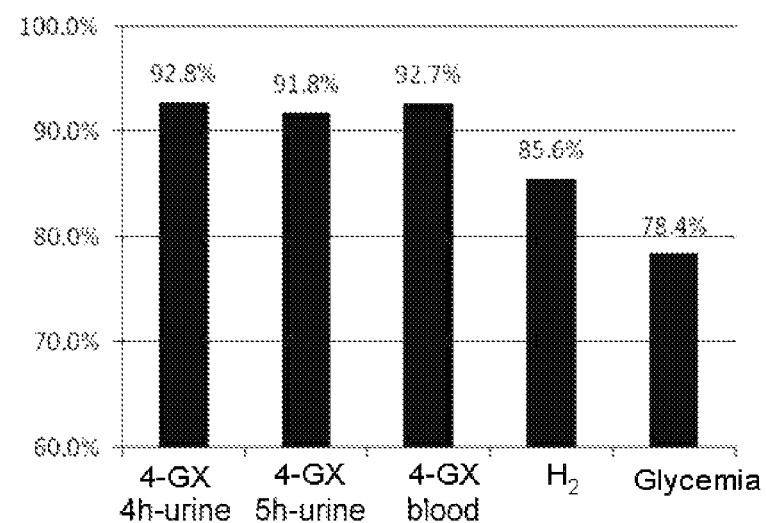
Figure 1:
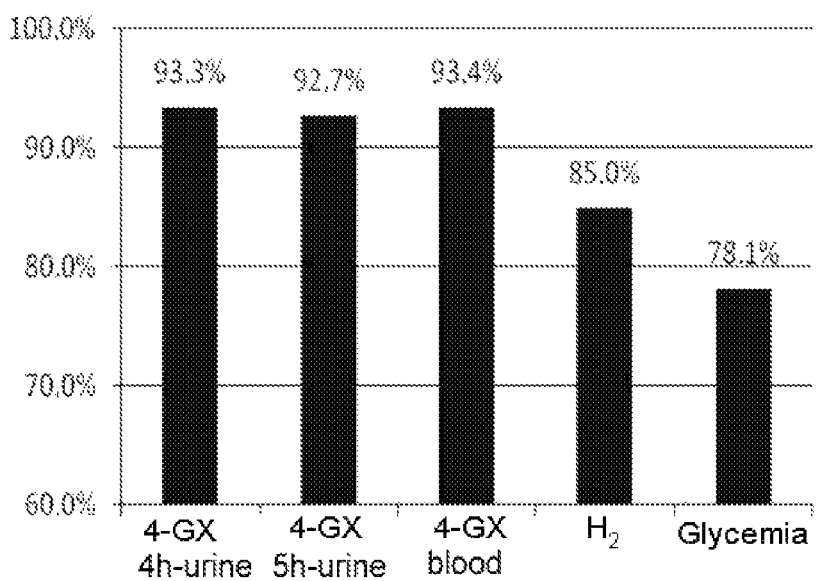
Figure 1:
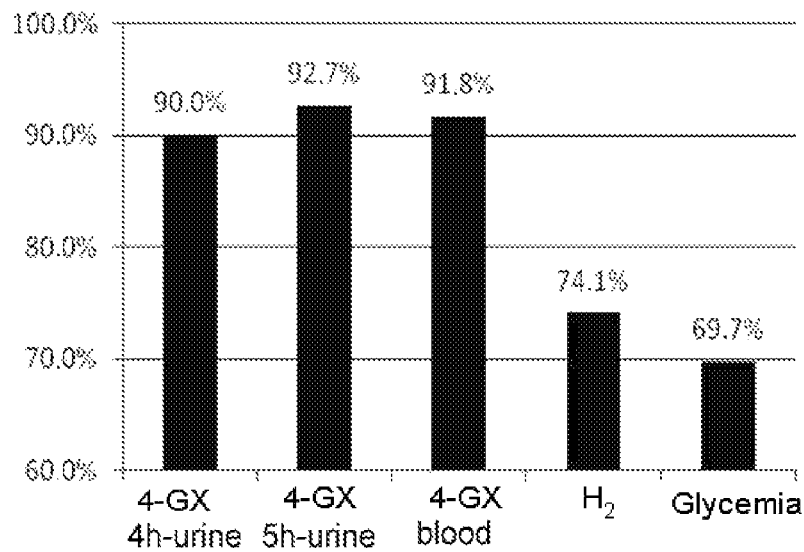
Figure 1:
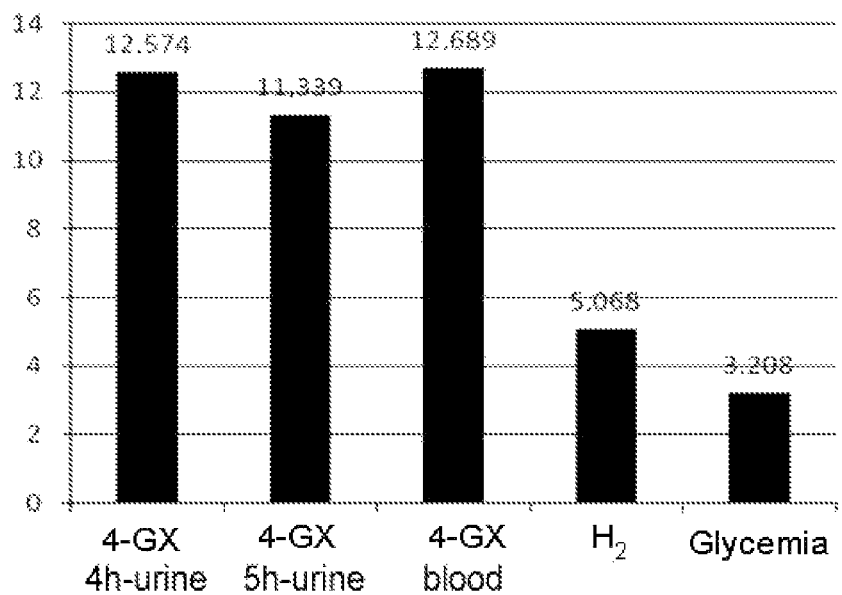
Figure 1:
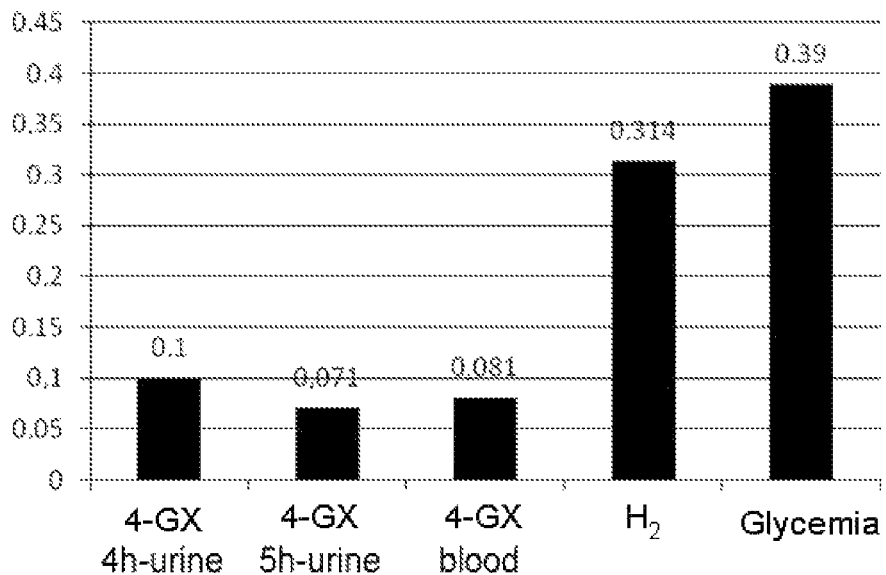

The present invention describes a non-invasive diagnostic method for intestinal lactase deficiency comprising the stages of:
  a) Administering via the oral route to the individual who is the object of the test a quantity of 4-GX of between 0.125 g and 6 g after a fasting period of at least 8 hours.
  b) Collecting total excreted urine by the individual between the time of administration of 4-GX and at least up to 4 hours following this administration.
  c) Determining in vitro the total amount of xylose excreted in the urine collected in this period of at least 4 hours following administration of 4-GX.
  d) Comparing the value obtained in step c) with a threshold reference value obtained in vitro from a population of healthy control individuals subjected to the same protocol, below which threshold value the subject is considered to be suffering from intestinal lactase deficiency.

In a preferred embodiment, the non-invasive diagnostic method for intestinal lactase deficiency by urine test is characterised in that in step b) the urine is collected over a period of at least 4 hours or at least up to 5 hours following administration of 4-GX.

In another preferred embodiment, the non-invasive diagnostic method for intestinal lactase deficiency by urine test is characterised in that the doses of 4-GX administered are selected from: 0.125 g, 0.250 g, 0.5 g, 1 g, 3 g and 6 g; the preferred dose to be administered being that of 0.5 g of 4-GX. It should be appreciated that the 4-GX doses can include small quantities of water which remain subsequent to the drying process of the 4-GX product. For example, the 4-GX product can contain about 8 wt % to about 12 wt %, most likely about 10 wt % water, based on the total weight of the product. Accordingly, the aforementioned 4-GX doses administered would actually include 0.1125 g, 0.225 g, 0.45 g, 0.9 g, 2.7 g and 5.4 g of actual 4-GX product, respectively, if they contain 10 wt % water.

In another preferred embodiment, the non-invasive diagnostic method for intestinal lactase deficiency by urine test is characterised in that the reference threshold value of the total quantity of xylose in urine at 4 h after the administration to the patient of a dose of 0.125 g of 4-GX (or 0.1125 g in a 4-GX sample including 10 wt % water) is 11.88 mg and in 5 h urine it is 16.72 mg.

In another preferred embodiment, the non-invasive diagnostic method for intestinal lactase deficiency by urine test is characterised in that the reference threshold value of the total quantity of xylose in urine at 4 h after the administration to the patient of a dose of 0.250 g of 4-GX (or 0.225 g in a 4-GX sample including 10 wt % water) is 20.62 mg and in 5 h urine it is 28.08 mg.

In another preferred embodiment, the non-invasive diagnostic method for intestinal lactase deficiency by urine test is characterised in that the reference threshold value of the total quantity of xylose in urine at 4 h after the administration to the patient of a dose of 0.5 g of 4-GX (or 0.45 g in a 4-GX sample including 10 wt % water) is 27.58 mg and in 5 h urine it is 37.87 mg.

In another preferred embodiment, the non-invasive diagnostic method for intestinal lactase deficiency by urine test is characterised in that the reference threshold value of the total quantity of xylose in urine at 4 h after the administration to the patient of a dose of 1 g of 4-GX (or 0.9 g in a 4-GX sample including 10 wt % water) is 33.04 mg and in 5 h urine it is 41.35 mg.

In another preferred embodiment, the non-invasive diagnostic method for intestinal lactase deficiency by urine test is characterised in that the reference threshold value of the total quantity of xylose in urine at 4 h after the administration to the patient of a dose of 3 g of 4-GX (or 2.7 g in a 4-GX sample including 10 wt % water) is 45.58 mg and in 5 h urine it is 69.57 mg.

In another preferred embodiment, the non-invasive diagnostic method for intestinal lactase deficiency by urine test is characterised in that the reference threshold value of the total quantity of xylose in urine at 4 h after the administration to the patient of a dose of 6 g of 4-GX (or 5.4 g in a 4-GX sample including 10 wt % water) is 87.96 mg and in 5 h urine it is 110.12 mg.

In another preferred embodiment, the non-invasive diagnostic method for intestinal lactase deficiency by urine test is characterised in that the comparison that takes place in step d) determines the degree of intestinal lactase deficiency (hypolactasia) in the individual subjected to the test.

Another object described in the present invention relates to a non-invasive diagnostic method for intestinal lactase deficiency comprising the stages of:
a) Extracting a blood sample from the individual who is the object of the test after fasting for 8 hours.
b) Administering via the oral route to the individual who is the object of the test a quantity of 4-GX of between 0.125 g and 6 g.
c) Extracting a blood sample from this individual at 90 minutes following administration of 4-GX.
d) Determining in vitro the concentration of xylose in the blood sample extracted in step a),
e) Determining in vitro the concentration of xylose in the blood sample extracted in step c).
f) Subtracting the values of in vitro xylose concentrations obtained in step e) from those obtained in step a).
g) Comparing the value obtained in step f) with a threshold reference value obtained in vitro from a population of healthy control individuals subjected to the same protocol, below which threshold the subject is considered to be suffering from intestinal lactase deficiency.

In a preferred embodiment, the non-invasive diagnostic method for intestinal lactase deficiency by blood test is characterised in that the determination of the concentration of xylose in the blood is preferably performed in plasma.

In another preferred embodiment, the non-invasive diagnostic method for intestinal lactase deficiency by blood test is characterised in that the doses of 4-GX administered are selected from: 0.5 g, 1 g, 3 g, and 6 g; the preferred dose to be administered being that of 3 g of 4-GX. It should be appreciated that the 4-GX doses can include small quantities of water which remain subsequent to the drying process of the 4-GX product. For example, the 4-GX product can contain about 8 wt % to about 12 wt %, most likely about 10 wt % water, based on the total weight of the product. Accordingly, the aforementioned 4-GX doses administered would actually include 0.45 g, 0.9 g, 2.7 g and 5.4 g of actual 4-GX product, respectively, if they contain 10 wt % water.

In another preferred embodiment, the non-invasive diagnostic method for intestinal lactase deficiency by blood test is characterised in that the reference threshold value of the concentration of xylose in blood after administration to the patient of the dose of 0.5 g of 4-GX (or 0.45 g in a 4-GX sample including 10 wt % water) is 0.41 mg/dL.

In another preferred embodiment, the non-invasive diagnostic method for intestinal lactase deficiency by blood test is characterised in that the reference threshold value of the concentration of xylose in blood after administration to the patient of the dose of 1 g (or 0.9 g in a 4-GX sample including 10 wt % water) of 4-GX is 0.53 mg/dL.

In another preferred embodiment, the non-invasive diagnostic method for intestinal lactase deficiency by blood test is characterised in that the reference threshold value of the concentration of xylose in blood after administration to the patient of the dose of 3 g (or 2.7 g in a 4-GX sample including 10 wt % water) of 4-GX is 0.97 mg/dL.

In another preferred embodiment, the non-invasive diagnostic method for intestinal lactase deficiency by blood test is characterised in that the reference threshold value of the concentration of xylose in blood after administration to the patient of the dose of 6 g of 4-GX (or 5.4 g in a 4-GX sample including 10 wt % water) is 1.44 mg/dL.

In another preferred embodiment, the non-invasive diagnostic method for intestinal lactase deficiency by blood test is characterised in that the comparison that takes place in step g) determines the degree of intestinal lactase deficiency (hypolactasia) in the individual subjected to the test.

Another of the objects of the present invention relates to 4-GX to be used as a reference test for the non-invasive diagnosis of intestinal lactase deficiency, being administered at doses of between 0.125 g and 6 g in a test of the total in vitro quantity of xylose in urine collected during a period of at least 4 hours after the administration of 4-GX. It should be appreciated that the 4-GX doses can include small quantities of water which remain subsequent to the drying process of the 4-GX product. For example, the 4-GX product can contain about 8 wt % to about 12 wt %, most likely about 10 wt % water, based on the total weight of the product. Accordingly, the aforementioned 4-GX doses administered would actually be between 0.1125 g and 5.4 g of actual 4-GX product, respectively, if they contain 10 wt % water.

In a preferred embodiment of the invention, 4-GX is used as a non-invasive reference test for the non-invasive diagnosis of intestinal lactase deficiency by urine test, the time for the collection of this urine being at least 5 hours following the administration of 4-GX.

In another preferred embodiment of the invention, 4-GX is used as a reference test for the non-invasive diagnosis of intestinal lactase deficiency by urine test, when it can be administered in any of the doses selected from: 0.125 g, 0.250 g, 0.5 g, 1 g, 3 g and 6 g (or 0.1125 g, 0.225 g, 0.45 g, 0.9 g, 2.7 g, and 5.4 g, respectively, in a 4-GX sample including 10 wt % water).

In another preferred embodiment of the invention, 4-GX is used in a reference test for the non-invasive diagnosis of intestinal lactase deficiency by urine test, when it can be preferably administered in a dose of 0.5 g (or 0.45 g in a 4-GX sample including 10 wt % water).

In a preferred embodiment of the invention, 4-GX is used in a reference test for the non-invasive diagnosis of intestinal lactase deficiency by urine test as previously indicated, comparing the value obtained in vitro of total xylose excreted in urine with a reference threshold value obtained in vitro in healthy control individuals subjected to the same reference test with 4-GX, this comparison determining the degree of intestinal lactase deficiency (hypolactasia).

Another object of the present invention relates to 4-GX to be used as a reference test for the non-invasive diagnosis of intestinal lactase deficiency, being administered at doses of between 0.125 g and 6 g in a test for the in vitro detection of the xylose concentration in blood obtained 90 minutes after the administration of 4-GX. It should be appreciated that the 4-GX doses can include small quantities of water which remain subsequent to the drying process of the 4-GX product. For example, the 4-GX product can contain about 8 wt % to about 12 wt %, most likely about 10 wt % water, based on the total weight of the product. Accordingly, the aforementioned 4-GX doses administered would actually be between 0.1125 g and 5.4 g of actual 4-GX product, respectively, if they contain 10 wt % water.

In a preferred embodiment of the invention, the determination of the concentration of xylose using 4-GX in a reference test for the non-invasive diagnosis of intestinal lactase deficiency is preferably performed in plasma.

In another preferred embodiment of the invention, 4-GX is used in a reference test for the non-invasive diagnosis of intestinal lactase deficiency by blood test, when it can be administered in any of the doses selected from: 0.5 g, 1 g, 3 g and 6 g (or 0.45 g, 0.9 g, 2.7 g, and 5.4 g, respectively, in a 4-GX sample including 10 wt % water).

In another preferred embodiment of the invention, 4-GX is used in a reference test in the non-invasive diagnosis of intestinal lactase deficiency by blood test, when it can be preferably administered in a dose of 3 g (or 2.7 g in a 4-GX sample including 10 wt % water).

In a preferred embodiment of the invention, 4-GX is used in a reference test in the non-invasive diagnosis of intestinal lactase deficiency by blood test as previously indicated, comparing the value obtained in vitro of xylose concentration in blood with a reference threshold value obtained in vitro in healthy control individuals subjected to the same reference test with 4-GX, this comparison determining the degree of intestinal lactase deficiency (hypolactasia).

The examples detailed below are for the purpose of illustrating the invention and do not limit its scope.

EXAMPLE 1

Sample Selection

Two groups of subjects were selected. A first group composed of 42 healthy controls and a second group composed of 205 subjects with a clinical history suggestive of lactose intolerance. Firstly, the lowest suitable oral dose of 4-GX administered to healthy volunteers was determined that enabled reliable detection (in terms of accuracy and reproducibility) of xylose levels in urine and blood via the analytical method to be used. In addition, the tolerance of these subjects to the various doses of 4-GX used in the test and the pharmacokinetics for each dose administered were analysed, both in urine and blood. The doses of 4-GX used were: 0.125 g, 0.250 g, 0.5 g, 1 g, 3 g and 6 g in addition to placebo in 12 healthy volunteers with washout period between doses of between three and seven days. It should be appreciated that the 4-GX doses can include small quantities of water which remain subsequent to the drying process of the 4-GX product. For example, the 4-GX product can contain about 8 wt % to about 12 wt %, most likely about 10 wt % water, based on the total weight of the product. Accordingly, the aforementioned 4-GX doses administered would actually include 0.1125 g, 0.225 g, 0.45 g, 0.9 g, 2.7 g and 5.4 g of actual 4-GX product, respectively, if they contain 10 wt % water. The study was performed with seven treatment periods and a washout time between the various periods of at least 3 days. In each study period, an ascending dose of 4-GX was administered and the serum and urine concentrations of xylose were measured at various times up to 8 hours following the administration of the drug.

The main measured variable was the quantity of xylose in urine collected following oral administration of 4-GX at the following times: basal, 0-1 h, 1-2 h, 2-3 h, 3-4 h, 4-5 h, 5-6 h, 6-7 h and 7-8 h. Secondary variables quantified were the plasma concentration of xylose measured in blood samples extracted following the oral administration of 4-GX at the following times: basal, 30 min, 60 min, 90 min, 120 min, 150 min, 3 h, 4 h, 5 h, 6 h, 7 h and 8 h. A pharmacokinetic analysis was also performed using the values of AUC (area under the curve of variation in the plasma xylose concentration against time), Cmax (maximum xylose plasma concentration), Tmax (time at which maximum xylose plasma concentration was reached) and $T_{1/2}$ (elimination half-life), calculated from the plasma concentrations of xylose derived from the hydrolysis of 4-GX by intestinal lactase.

The data obtained in the test by the administration of 4-GX in the group of healthy controls was used to determine the optimum doses and times for determining if a patient showed lactose intolerance by the method described in the present invention and also the lower limits of normal of xylose in urine and blood (cut-off points) for each of the doses used. The indicator of the lower limit of normal was taken to be the difference between the average xylose concentrations in blood and/or the difference between the average total amounts of xylose excreted in the urine, and 1.96 times the standard deviation.

Once the normal lower limits of xylose in healthy subjects had been obtained, 205 subjects with a clinical history suggestive of lactose intolerance were subjected to the various diagnostic tests for lactose intolerance in the state of the art in order to compare with the results obtained by the diagnostic test of lactose intolerance by the oral administration of 4-GX. The diagnostic tests to which these patients were subjected were:

Intestinalbiopsy: determining intestinal lactase activity therein.

Hydrogenbreathtest after the oral administration to patients of 50 g of lactose. While this test was being carried out, several capillary-bloodglucosetest(Glycemiatests) were carried out, calculating the highest increase observed in the blood glucose concentration compared to basal glucose level before starting the test.

4-GXtestintotalurineat0-4and0-5hours,whichwasorally administeredtopatients0.5gofthisproduct(or0.45gina4-GXsampleincluding10wt%water), collecting the total urine accumulated over 0-4 h and 0-5 h following the administration of 4-GX and determining the amount of excreted xylose in both volumes of urine.

4-GXtestinbloodwhich was orally administered to patients 3 g of this product (or 2.7 g in a 4-GX sample including 10 wt % water) to determine the concentration of plasma xylose in a blood sample 90 minutes after ingestion of the product. The concentration obtained was compared to a basal blood sample extracted before ingestion of 4-GX.

The 4-GX was orally administered in a single dose dissolved in 100 ml of water. To demonstrate the effectiveness, specificity and sensitivity of the intestinal lactase test by the administration of the above indicated doses of 4-GX in subjects with a clinical history suggestive of lactose intolerance, the results obtained via these tests were compared with the results obtained with the other tests: Biopsy, hydrogen breath test and capillary-blood glucose test after a lactose overload.

EXAMPLE 2

Selection of the Optimum Dose and Time for the Diagnosis of Lactose Intolerance by the Oral Administration of 4-GX The main pharmacokinetic parameters that were evaluated for urine excretion of xylose were the maximum rate of urinary excretion (U rate max) and the total quantity of xylose excreted over the period of observation (Ae 0-t); using the amounts of xylose excreted in each urine sample collection period, the quantities accumulated for each interval were calculated so that it was possible to determine the minimum urine collection time that would distinguish accumulated excretion at the various doses compared to placebo (Table 1).

The statistical analysis of the pharmacokinetic parameters of urinary xylose excretion showed that all the doses of 4-GX, in terms of the maximum urinary excretion rate (U rate max) and accumulated excretion over 8 hours of duration of the observation period (Ae 0-t) were significantly different from that obtained with placebo. The analysis of the quantities accumulated over the observation period for the various doses showed that the lowest dose of 4-GX for which significant differences in total xylose excretion compared to placebo could be determined was the dose of 0.5 g (or 0.45 g in a 4-GX sample including 10 wt % water) (amount accumulated at 8 hours was 25.52 mg; CI 9.82-41.82) and that this difference could be observed in the urine collection period of between 3 and 4 hours (amount accumulated at 4 hours was 57.24 mg; IC95%: 46.66-67.82) (Table 2) and was still more evident in the interval between 4 and 5 hours (amount accumulated at 5 hours was 65.05 mg; IC95%: 53.81-73.04) (Table 2). Therefore, it can be concluded that significant differences in the accumulated xylose excreted, compared to placebo, can be detected by measuring the accumulated excretion in urine at least 4 hours after administration of a dose of 0.5 g of 4-GX (or 0.45 g in a 4-GX sample including 10 wt % water).

TABLE 1

Summary of kinetic parameters of xylose concentration excreted in urine at different 4-GX doses.

| | Placebo | 0.125 g | 0.250 g | 0.5 g | 1 g | 3 g | 6 g |
|---|---|---|---|---|---|---|---|
| U rate Max (mg/h) * | 4.49 (2.04) | 9.14 (2.90) | 14.01 (3.82) | 18.67 (5.96) | 26.69 (7.56) | 52.02 (21.83) | 82.81 (30.46) |
| Ae 0-t * (mg/dl/h) | 18.34 (7.67) | 41.45 (7.52) | 63.97 (13.91) | 80.15 (19.65) | 112.32 (38.79) | 207.82 (95.89) | 315.74 (96.71) |
| Tmax U rate (h) ** | 0.5 (0.5-5.5) | 2.0 (0.5-7.5) | 1.5 (0.5-2.5) | 1.5 (0.5-2.5) | 2.5 (1.5-2.5) | 1.5 (1.5-3.5) | 2.0 (1.5-2.5) |
| T1/2 (h) * | 3.35 (1.90) | 3.53 (1.59) | 3.77 (2.09) | 2.50 (1.49) | 2.43 (0.44) | 1.93 (0.77) | 3.06 (1.90) |

* Expressed as mean (standard deviation)
** Expressed as median (range)
U rate Max (mg/h): Maximum urinary excretion rate
Ae 0-t (mg/dL/h): accumulated xylose excretion over the 8 hours duration of the observation period.
Tmax U rate (h): time to reach the maximum xylose concentration excreted in urine
T1/2 (h): xylose elimination half-life in urine

TABLE 2

Average amount (mg) of xylose accumulated in urine in each urine collection period for each administered dose. The 95% confidence interval (CI 95%) is shown.

| Dose (mg) | | 0-1 h | 1-2 h | 2-3 h | 3-4 h | 4-5 h | 5-6 h | 6-7 h | 7-8 h |
|---|---|---|---|---|---|---|---|---|---|
| 0 | Mean | 3.90 | 6.20 | 8.68 | 11.41 | 14.47 | 17.91 | 21.67 | 25.82 |
| | lower CI | 2.29 | 4.17 | 6.37 | 8.46 | 10.16 | 11.17 | 11.02 | 9.82 |
| | upper CI | 5.51 | 8.23 | 10.99 | 14.37 | 18.78 | 24.65 | 32.31 | 41.82 |
| 125 | Mean | 6.81 | 12.80 | 19.29 | 25.62 | 30.45 | 34.51 | 38.34 | 41.45 |
| | lower CI | 5.01 | 10.54 | 16.51 | 21.48 | 26.14 | 30.06 | 33.42 | 36.67 |
| | upper CI | 8.62 | 15.06 | 22.07 | 29.77 | 34.76 | 38.96 | 43.26 | 46.23 |
| 250 | Mean | 8.44 | 20.59 | 32.48 | 41.03 | 48.37 | 54.49 | 59.68 | 63.97 |
| | lower CI | 6.45 | 16.93 | 27.38 | 34.05 | 40.89 | 46.44 | 51.07 | 55.13 |
| | upper CI | 10.44 | 24.24 | 37.57 | 48.01 | 55.84 | 62.54 | 68.29 | 72.81 |
| 500 | Mean | 13.47 | 31.13 | 46.37 | 57.24 | 65.05 | 71.23 | 75.86 | 80.15 |
| | lower CI | 10.48 | 24.69 | 37.09 | 46.66 | 53.81 | 59.39 | 63.89 | 67.66 |
| | upper CI | 16.45 | 37.56 | 55.64 | 67.82 | 76.29 | 83.06 | 87.83 | 92.64 |
| 1000 | Mean | 17.49 | 41.24 | 65.04 | 79.60 | 92.10 | 100.55 | 106.78 | 112.32 |
| | lower CI | 12.83 | 31.36 | 52.95 | 63.74 | 73.04 | 79.11 | 83.62 | 87.67 |
| | upper CI | 22.16 | 51.11 | 77.13 | 95.47 | 111.16 | 121.99 | 129.93 | 136.98 |
| 3000 | Mean | 25.98 | 70.29 | 110.98 | 114.16 | 168.95 | 187.57 | 199.17 | 207.82 |
| | lower CI | 15.09 | 43.40 | 74.64 | 100.74 | 119.18 | 131.69 | 141.10 | 146.88 |
| | upper CI | 36.87 | 97.18 | 147.33 | 187.59 | 218.71 | 243.45 | 257.24 | 268.76 |

TABLE 2-continued

Average amount (mg) of xylose accumulated in urine in each urine collection period for each administered dose. The 95% confidence interval (CI 95%) is shown.

| Dose (mg) | | 0-1 h | 1-2 h | 2-3 h | 3-4 h | 4-5 h | 5-6 h | 6-7 h | 7-8 h |
|---|---|---|---|---|---|---|---|---|---|
| 6000 | Mean | 30.04 | 99.36 | 173.64 | 228.07 | 266.89 | 285.99 | 304.94 | 315.74 |
| | lower CI | 19.25 | 72.71 | 136.54 | 180.90 | 212.27 | 228.61 | 244.60 | 254.27 |
| | upper CI | 40.63 | 126.01 | 210.74 | 275.24 | 321.52 | 343.37 | 365.28 | 377.20 |

The next objective was the determination and pharmacokinetic analysis of the xylose concentration in plasma in order to identify the smallest dose of 4-GX that could be distinguished from placebo (without 4-GX administration) to be used in the 4-GX test for the diagnosis of intestinal lactase deficiency (Table 3).

For all administered doses, maximum concentrations of plasma xylose appeared between 1 and 2 hours following oral administration of 4-GX (median 90 minutes). Differences compared to placebo, possibly significant from the clinical point of view, started to appear from the dose of 1 g (or 0.9 g in a 4-GX sample including 10 wt % water) (Cmax for 1 g was 5.44±0.68 mg/dl; IC90%: 124.63-135.65) (Table 4). Applying a confidence interval of 95%, more demanding and therefore more precise, these observed differences compared to placebo reduced slightly, being feasible that the dose of 1 g was not sufficient to obtain discriminatory power in almost all cases to be used as a diagnostic tool (CI95%: 123.59-136.78). The dose of 3 g (or 2.7 g in a 4-GX sample including 10 wt % water) showed a Cmax of 6.08±0.73 mg/dl, and the 90% confidence interval compared to placebo showed better discriminatory power (CI90%: 139.36-151.38) (Table 4), which was also maintained after calculating the 95% confidence interval (CI95%: 138.20-152.95), for which reason it seemed more reasonable to select this dose for subsequent clinical development of 4-GX as a diagnostic test for lactase deficiency.

TABLE 4

Summary of the statistical analysis of the concentration of xylose in plasma compared to placebo following 4-GX administration.

| VARIABLE | Dose | RATIO | $IC^{90\%}$ | |
|---|---|---|---|---|
| Ln Cmáx | 0.125 g | 109.45 | 104.90 | 114.18 |
| | 0.250 g | 117.91 | 113.02 | 123.02 |
| | 0.5 g | 123.95 | 118.80 | 129.31 |
| | 1 g | 130.02 | 124.63 | 135.65 |
| | 3 g | 145.39 | 139.36 | 151.68 |
| | 6 g | 167.51 | 160.56 | 174.76 |
| Ln $AUC_{0-t}$ | 0.125 g | 102.21 | 98.55 | 106.01 |
| | 0.250 g | 107.72 | 103.86 | 111.72 |
| | 0.5 g | 111.72 | 107.72 | 115.87 |
| | 1 g | 114.69 | 110.59 | 118.95 |
| | 3 g | 123.27 | 118.86 | 127.85 |
| | 6 g | 130.08 | 125.42 | 134.91 |

Ln Cmax: Neperian logarithm of the maximum plasma xylose concentration.
Ln $AUC_{0-t}$: Neperian logarithm of the area under the curve of variation in the plasma xylose concentration against time.

In view of the results, it can be concluded that: the lowest dose of 4-GX for which the excretion of xylose in urine can be reliably distinguished from placebo is 0.5 g (or 0.45 g in a 4-GX sample including 10 wt % water) and the time required for urine collection should be at least 4 hours in order to assure collection of a sufficient quantity of excreted xylose. The highest concentrations of xylose in plasma obtained using different doses of 4-GX suggest that the

TABLE 3

Summary of kinetic parameters of xylose concentration in blood at different 4-GX doses.

XYLOSE

| | Placebo | 0.125 g | 0.250 g | 0.5 g | 1 g | 3 g | 6g |
|---|---|---|---|---|---|---|---|
| Cmax* | 4.17 | 4.58 | 4.92 | 5.18 | 5.44 | 6.08 | 7.02 |
| (mg/dl) | (0.39) | (0.59) | (0.50) | (0.55) | (0.68) | (0.73) | (0.91) |
| AUC 0-t* | 31.77 | 32.49 | 34.25 | 35.53 | 36.60 | 39.24 | 41.39 |
| (mg/dl/h) | (3.11) | (3.43) | (3.68) | (3.88) | (4.99) | (4.60) | (4.69) |
| Tmax** | 1.0 | 1.0 | 1.5 | 1.5 | 1.5 | 1.5 | 1.5 |
| (h) | (0.0-6.0) | (0.5-1.5) | (0.5-2.0) | (1.5-2.0) | (0.5-3.0) | (1.0-2.0) | (1.5-2.0) |
| T1/2* (h) | 38.91 | 27.28 | 30.52 | 24.64 | 15.3 | 17.21 | 9.64 |
| | (28.7) | (9.28) | (28.44) | (14.63) | (4.60) | (21.59) | (3.46) |

*Expressed as mean (standard deviation)
**Expressed as median (range)
Cmax: maximum plasma xylose concentration
AUC 0-t (mg/dL/h): area under the curve of variation in the plasma xylose concentration against time
Tmax (h): time to achieve the maximum plasma xylose concentration
T1/2 (h): xylose elimination half-life.

lowest dose for which significant differences compared to placebo can be distinguished is 3 g (or 2.7 g in a 4-GX sample including 10 wt % water) and the determination of plasma xylose concentration should be at 90 minutes following oral administration of 4-GX.

EXAMPLE 3

Determination of the Lower Limits of Normal of the Total Quantity of Xylose Excreted in Urine and Blood Concentration in Healthy Control Individuals The data obtained with the 4-GX administration test in the healthy control group was used to determine the lower limits of normal of xylose in urine and blood (cut-off points). The cut-off points for the 4-GX test in urine were obtained for times of 4 hours and 5 hours because, as already seen in example 2, these times are the best for determining the amount of xylose excreted in urine following 4-GX administration and performing a reliable diagnosis of lactase deficiency. Similarly, the cut-off points for the determination of the blood xylose concentration following 4-GX administration were obtained for the time of 90 minutes following ingestion of the disaccharide. The difference between the average xylose concentration (in blood and the total quantity of xylose excreted in the urine) and 1.96 times the standard deviation was used for the lower limit of normal indicator. The results obtained are shown in Table 5. The lower limit of xylose accumulated in 4-hour urine was 27.58 mg; xylose accumulated in 5-hour urine was 37.87 mg and the increase in the concentration of plasma xylose after 90 minutes following ingestion of the product, compared to basal blood, was 0.97 mg/dL.

Subjects participating in the study who presented levels of xylose below these normal limits were considered as positive, i.e. these levels are indicative of intestinal lactase deficiency, the cause of the clinical symptoms of lactose intolerance.

TABLE 5

Cut-off points of the three diagnostic tests for intestinal lactase deficiency by the use of different doses of 4-GX.

| Diagnostic test | 4-GX (g) | Cut-off point |
|---|---|---|
| 4-hour urine | 0.125 | 11.88 mg |
|  | 0.250 | 20.62 mg |
|  | 0.5 | 27.58 mg |
|  | 1 | 33.04 mg |
|  | 3 | 45.58 mg |
|  | 6 | 87.96 mg |
| 5-hour urine | 0.125 | 16.72 mg |
|  | 0.250 | 28.08 mg |
|  | 0.5 | 37.87 mg |
|  | 1 | 41.35 mg |
|  | 3 | 69.75 mg |
|  | 6 | 110.12 mg |
| 90-min blood | 0.5 | 0.41 mg/dL |
|  | 1 | 0.53 mg/dL |
|  | 3 | 0.97 mg/dL |
|  | 6 | 1.44 mg/dL |

EXAMPLE 4

Determination of the Total Amount of Xylose Excreted in Urine in Subjects with a Clinical History Suggestive of Lactose Intolerance Having obtained the lower limits of normal or cut-off points for each of the doses and the optimum times used in the present invention, the total amounts of xylose excreted in urine of subjects with a clinical history suggestive of lactose intolerance were measured. From here on, the optimum dose of 0.5 g of 4-GX (or 0.45 g in a 4-GX sample including 10 wt % water) was used in the 4-GX urine test for the diagnosis of intestinal lactase deficiency by the non-invasive method described in the present invention. This dose was dissolved in 100 ml water, and following the test protocol, 2 samples of urine excreted during the 5 hours following the administration of the drug were taken, in two interval groups: at 4 hours following administration of 4-GX and at 5 hours following administration of 4-GX.

EXAMPLE 5

Determination of the Blood Xylose Concentration in Subjects with a Clinical History Suggestive of Lactose Intolerance In the same way as the case for the determination of the amount of xylose excreted in urine described in the previous example, for the determination of xylose concentrations in blood, 3 g of 4-GX (or 2.7 g in a 4-GX sample including 10 wt % water) dissolved in approximately 100 ml water was administered to patients with a clinical history suggestive of lactose intolerance and to healthy volunteers, and according to the test protocol, 2 samples of blood were taken at the following times: basal (before the administration of the drug) and at 90 minutes following administration of 4-GX. The blood samples were centrifuged to obtain plasma in which the analysis of the amount of xylose present was performed.

EXAMPLE 6

Statistical and Analytical Method

From the data obtained from the various urine tests for intestinal lactase deficiency following oral ingestion of 4-GX described in the present invention, a descriptive statistical analysis was performed of the amount of xylose excreted in the urine up to 4 hours and up to 5 hours following said administration. The same was done with the blood test for intestinal lactase activity following oral ingestion of 4-GX, where descriptive statistical analysis was performed on the amount of xylose present in the plasma of subjects at 90 minutes following administration of 4-GX. The net increase in the plasma xylose concentration compared to basal values was also calculated.

The results were expressed as mean, standard deviation, maximum value, median value and minimum value. The 95% confidence intervals were also calculated for each of the analysed variables. The statistical package SPSS v14.0 (SPSS Inc., Chicago) was used for data analysis.

EXAMPLE 7

Measurement of Intestinal Lactase Activity with the 4-GX Test Described in the Invention and Comparison of the Results Obtained Using this Test with Those Obtained Using the Intestinal Biopsy Test, Hydrogen Breath Test and Capillary-blood Glucose Test To obtain the statistical parameters of lactase determination using the various 4-GX tests described in the present invention and later to compare them with the results obtained from the intestinal biopsy test, hydrogen in exhaled air test and capillary-blood glucose test, the normal limits of the measurement of the total amount of xylose excreted in 4-hour and 5-hour urine and the concentration of blood xylose after 90 minutes following ingestion of 4-GX described in Table 5 were used. The normal limits for the other tests were those used in common clinical practice for the diagnosis of lactose intolerance (Arola, H. (1994) Diagnosis of hypolactasia and lactose malabsorption. Scand. J. Gastroenterol. 20229 (Suppl), 26-35), which are:

For the measurement of lactasebyintestinalbiopsy, the lower normal limit is established at 10 units/g protein, with values less than this being considered positive.

For the hydrogenbreathtest, the normal limit is established at 20 ppm (parts per million) as the maximum peak value compared to the basal value during the performance of the test, with values higher than this being considered as positive.

For the capillary-bloodglucosetest, the normal limit is established as an increase of 25 mg/dL as a maximum peak compared to the basal value during the hydrogen breath test.

Taking these normal limits into account, an analysis of intestinal lactase deficiency in the 205 patients enrolled in the study was performed using the various techniques described above. The results obtained are shown in Table 6. As shown in Table 6, the intestinal biopsy test detected 52.7% of the 205 subjects studied as being positive (those presenting intestinal lactase deficiency), while some 47.3% of these subjects had normal levels of the enzyme. The intestinal lactase test using 4-GX administration and measuring 4-hour urine showed that 51.2% of the patients presented intestinal lactase deficiency, whereas the 4-GX and 5-hour urine test showed that 53.2% of the patients were positive. Using the 4-GX and blood test, the proportion of patients presenting intestinal lactase deficiency was 51.7%. The percentages of patients presenting intestinal lactase deficiency using the other two tests, the hydrogen breath test and the capillary-blood glucose test, were less than those obtained by the tests mentioned above, that is 45% and 47% respectively.

TABLE 6

Percentages of patients presenting intestinal lactase deficiency by the various diagnostic tests and applying the normal limits described above.

| | No. Positive | No. Negative |
|---|---|---|
| Intestinal biopsy test | 108 (53%) | 97 (47%) |
| 4-GX test in 4-hour urine | 105 (51%) | 100 (49%) |
| 4-GX test in 5-hour urine | 109 (53%) | 96 (47%) |
| 4-GX test in 90-minutes blood | 106 (52%) | 97 (48%) |
| Hydrogen breath test | 93 (45%) | 112 (55%) |
| Capillary-blood glucose test | 96 (47%) | 109 (53%) |

The tests performed in this study (biopsy, 4-GX and 4-hour urine, 4-GX and 5-hour urine, 4-GX and blood, hydrogen breath test and capillary-blood glucose test) are for diagnosing intestinal lactase deficiency or hypolactasia by the measurement of variables that, directly or indirectly, reflect enzyme activity. Therefore the criteria for positive diagnosis are established exclusively from normal cut-off points for each test. The cut-off points are independent of gender, age and race.

The results obtained in each of the tests performed on these patients after analysing the data are shown in the form of statistical parameters in Table 7.

TABLE 7

Statistical parameters calculated after analysing the data obtained from the different tests performed and considering the measurement of lactase in intestinal biopsy as the gold standard test in each case.

| | | CI 95% |
|---|---|---|
| 4-GX test in 4-hour urine | | |
| Sensitivity (%) | 90.74 | 83.63 to 95.47 |
| Specificity (%) | 92.78 | 85.70 to 97.05 |
| Positive predictive value (%) | 93.33 | 86.75 to 97.28 |
| Negative predictive value (%) | 90.00 | 82.38 to 95.10 |
| 4-GX test in 5-hour urine | | |
| Sensitivity (%) | 93.52 | 87.10 to 97.35 |
| Specificity (%) | 91.75 | 84.39 to 96.37 |
| Positive predictive value (%) | 92.66 | 86.05 to 96.78 |
| Negative predictive value (%) | 92.71 | 85.55 to 97.02 |
| 4-GX blood test | | |
| Sensitivity (%) | 92.52 | 85.80 to 96.72 |
| Specificity (%) | 92.71 | 85.55 to 97.02 |
| Positive predictive value (%) | 93.40 | 86.87 to 97.30 |
| Negative predictive value (%) | 91.75 | 84.39 to 96.37 |
| Hydrogen breath test | | |
| Sensitivity (%) | 73.15 | 63.76 to 81.22 |
| Specificity (%) | 85.57 | 76.97 to 91.88 |
| Positive predictive value (%) | 84.95 | 76.03 to 91.52 |
| Negative predictive value (%) | 74.11 | 64.97 to 81.92 |
| Capillary-blood glucose test | | |
| Sensitivity (%) | 69.44 | 59.84 to 77.95 |
| Specificity (%) | 78.35 | 68.83 to 86.07 |
| Positive predictive value (%) | 78.13 | 68.53 to 85.92 |
| Negative predictive value (%) | 69.72 | 60.19 to 78.16 |

CI: confidence interval.

The values and percentages of sensitivity (A), specificity (B), positive predictive value (C) and negative predictive value (D) of the tests (intestinal lactase deficiency diagnostic test described in the present invention, hydrogen breath test and capillary-blood glucose test) performed in patients with clinical history suggestive of lactose intolerance following the administration of the different doses of 4-GX compared to the determination of intestinal lactase activity in biopsy taken as the gold standard test are shown in Table 7 and in FIG. 1. All the values of sensitivity, specificity, positive predictive value and negative predictive value obtained using the intestinal lactase test with 4-GX, and both urine and blood tests, are greater than 90%, which indicates high reliability of any of these three new diagnostic tests using 4-GX, whether this involves the determination of the concentration of xylose in plasma or the determination of the amount of xylose excreted in urine after two different times.

The best indicator of the high reliability of these diagnostic tests using the disaccharide 4-GX is to compare the values obtained in the test of the invention with the values obtained in the hydrogen breath test and the capillary-blood glucose test, which are the most common non-invasive tests currently used in the clinic for the diagnosis of intestinal lactase deficiency. Table 7 shows that the values for sensitivity, specificity, positive predictive value and negative predictive value for the hydrogen breath test varied around 73-85% and the values for the capillary-blood glucose test varied around 69-78%, never reaching the values shown by any of the 4-GX tests, which in all cases were above 90%.

All the statistical parameters of the hydrogen breath test and the capillary-blood glucose test presented values and ranges (95% confidence intervals) that were considerably lower than that of any of the 4-GX tests (Table 7). The sensitivity of the hydrogen breath test was 73.2% (percentage of true positives), which is equivalent to saying that this test presented 26.8% false negatives (percentage of patients that being hypolactasic according to the measurement of lactase in biopsy were not detected as such in this test), whereas the sensitivity of the 4-GX tests was 90.7% (4-hour urine), 93.5% (5-hour urine) and 92.5% (blood), that is 9.3%, 6.5% and 7.5% false negatives respectively (FIG. 1A).

The specificity of the hydrogen breath test was 85.6% (percentage of true negatives), which is equivalent to saying that this test presented 14.4% false positives (percentage of patients testing positive in this test that are not hypolactasic according to the measurement of lactase in biopsy), whereas the sensitivity of the 4-GX tests was 92.8% (4-hour urine), 91.8% (5-hour urine) and 92.7% (blood), that is 7.2%, 8.2% and 7.3% false positives respectively (FIG. 1B).

Equally, the positive predictive value (percentage of true positives compared to total positives) and the negative predictive value (percentage of true negatives compared to total negatives) were clearly less with the hydrogen breath test, 85% and 74.1% respectively, compared to 93.3% (4-hour urine), 92.7%, (5-hour urine) and 93.4% (blood) of the positive predictive values for the 4-GX tests (FIG. 1C) and 90% (4-hour urine), 92.7% (5-hour urine) and 91.8% (blood) of the negative predictive values for the 4-GX tests (FIG. 1D).

Also, the positive likelihood ratio (FIG. 1E) obtained for the hydrogen breath test was 5.068, whereas with the 4-GX test it varied between 11.339 and 12.574, which indicates that the probability that a positive result obtained by the determination of lactase by biopsy is also positive with any of the 4-GX tests is even twice as high as with the hydrogen breath test.

The likelihood ratio of a negative result (FIG. 1F) was 0.314 with the hydrogen breath test, whereas with the 4-GX tests it varied between 0.071 and 0.100, which indicates the probability that a positive result obtained by determination of lactase by biopsy is negative with any of the 4-GX tests is even three times less than with the hydrogen breath test.

The comparison of the data obtained by the various 4-GX tests of the invention compared to the hydrogen breath test was also made by looking at the area under the corresponding ROC (Receiver-Operating Characteristic) curves, which are curves indicating the accuracy of a diagnostic test. In these curves, a test is considered as optimum when the area under the curve approaches the value of 1, at which value the sensitivity and the specificity of the candidate test are both 100%.

Figure 2:
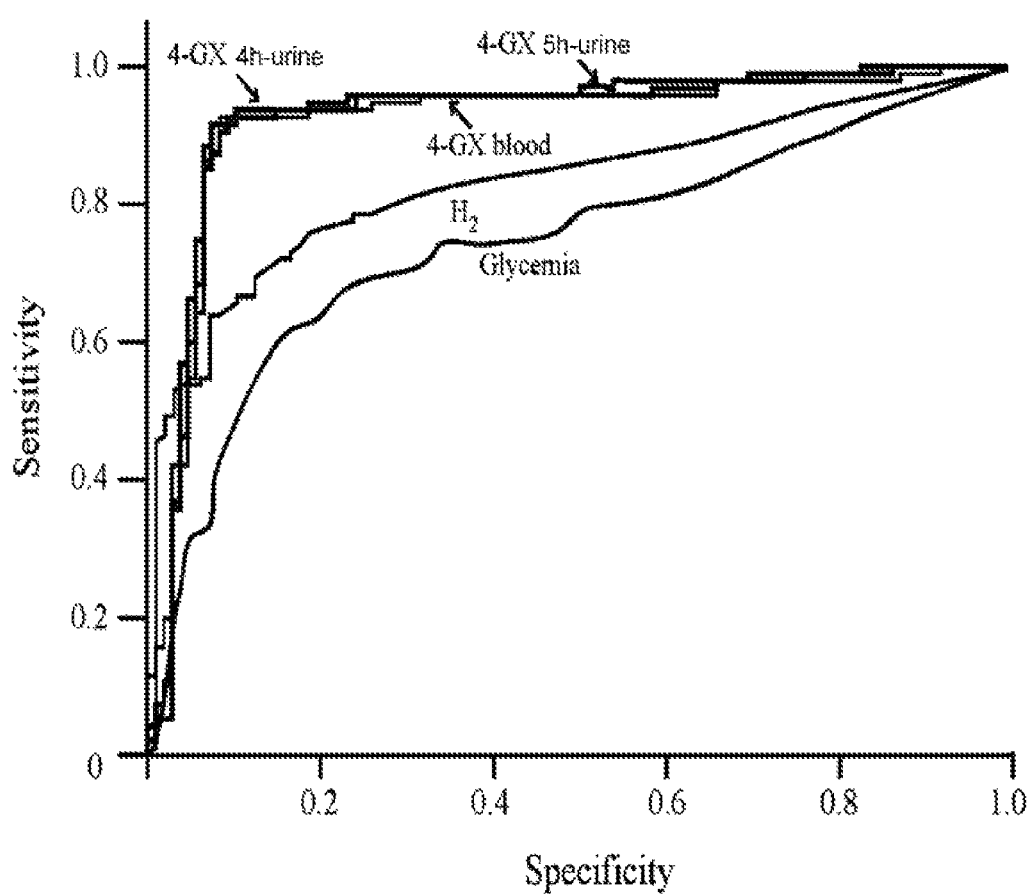
FIG. 2. ROC curves ("Receiver-Operating-Characteristic", indicating the accuracy of a diagnostic test) of the various tests performed in patients (n=205) with symptoms suggestive of lactose intolerance after the administration of different doses of 4-GX compared to the determination of intestinal lactase activity in biopsy taken as the gold standard.

In the case of the hydrogen breath test, this area was 0.8501 (FIG. 2), whereas the area obtained with the 4-GX tests was 0.9282 for the case of the concentration of xylose excreted in 4-hour urine, 0.9315 for the case of the concentration of xylose excreted in 5-hour urine and 0.9268 for the xylose concentration in blood (FIG. 2). This difference in the area under the ROC curves is displayed by the marked displacement towards the right of the ROC curve of the hydrogen breath test compared to the other curves corresponding to the 4-GX tests of the present invention, also showing a statistical significance level of $p<0.05$ compared to the hydrogen breath test.

The sensitivity and specificity of a diagnostic test can also be calculated from ROC curves. The values for sensitivity and specificity of the diagnostic tests of intestinal lactase deficiency by the use of 4-GX using the ROC curves were 90.7% and 93.8% respectively for the 4-GX test and 4-hour urine samples; 93.5% and 91.8% respectively for the 4-GX and 5-hour urine test samples; and 92.5% and 92.7% respectively for the 4-GX and blood test samples. These values are almost identical to those previously described for the same parameters [sensitivity of 90.7% and 92.8% respectively (4-hour urine), 93.5% and 91.8% respectively (5-hour urine), and 92.5% and 92.7% respectively (blood)] calculated using the cut-off points previously described, which confirms the validity of these cut-off points for the diagnosis of patients presenting lactose intolerance.

As regards the determination of capillary-blood glucose, as shown in FIG. 1, the statistical parameters were of the same order as those obtained with the hydrogen breath test and less than those obtained with the 4-GX tests. The sensitivity of the capillary-blood glucose test was 69.4%, i.e. 30.6% were false negatives, whereas the sensitivity of the 4-GX tests varied between 90.7% and 93.5%. The specificity of the capillary-blood glucose test was 78.4%, which indicates that there were 21.6% of false positive results, whereas the specificity of the 4-GX tests of the invention varied from 91.8% to 92.8%. The positive and negative predictive values for the capillary-blood glucose test were 78.13% and 69.72% respectively, whereas the 4-GX tests these values varied between 92.66% and 93.40% and from 90.00% to 92.71% respectively.

Lastly, the positive and negative likelihood ratios for the capillary-blood glucose test were 3.208 and 0.390 respectively, whereas for the 4-GX tests these parameters varied from 11.339 to 12.689 and 0.071 to 0.100 respectively. Therefore, as in the case of the hydrogen breath test, the values for sensitivity, specificity, positive predictive value and negative predictive value for the capillary-blood glucose test and for the hydrogen breath test did not reach the values shown with any of the different 4-GX tests, which in all cases were higher than 90%.

EXAMPLE 8

Analysis of the Discordant Results Obtained Between the Intestinal Biopsy Test and 4-GX Intestinal Lactase Test in Patients with a Clinical History Suggestive of Lactose Intolerance Once the results from patients presenting clinical history suggestive of lactose intolerance were obtained by the intestinal biopsy technique and the 4-GX tests, it was observed that there were subjects for which discrepancies in diagnosis were found using the normal limits of each the techniques used. Table 8 shows the subjects in which discrepancies in diagnosis were observed, taking into account the normal limit of the biopsy test and the normal limits of the 4-GX tests described in the present invention. Table 8 also shows the results of the other two diagnostic tests used in this study, the hydrogen breath test and the capillary-blood glucose test, and the number of discrepant results shown by each subject between the results obtained by the intestinal biopsy test compared to the other diagnostic tests performed.

TABLE 8

Results obtained in patients where there was a discrepancy between the values of lactase measured in biopsy and those obtained by the other tests performed. The limits of normal of each test are included, indicating normal as being greater than or equal (≥) or less than or equal (≤). The data of each test that was positive are represented as dark grey shaded and those that were negative are represented as light grey shaded.

| Normal limits | ≥ 10 U/g prot. | ≥ 27.58 mg | ≥ 37.87 mg | ≥ 0.97 mg/dL | ≤ 20 ppm | ≥ 25 mg/dL | |
|---|---|---|---|---|---|---|---|
| Patient | Biopsy (Ug/prot.) | 4-GX 4-hour urine (mg) | 4-GX 5-hour urine (mg) | 4-GX blood (mg/dL) | H₂ breath test (ppm) | Glycemia test (mg/dL) | Difference |
| A03 | 10.12 | 23.868 | 29.579 | 0.485 | 69 | 0 | 5 |
| I58 | 12.47 | 26.912 | 35.776 | 0.294 | 62 | 14 | 5 |
| I55 | 17.26 | 27.558 | 34.406 | 0.257 | 55 | 11 | 5 |
| C12 | 12.15 | 21.971 | 30.497 | 0.751 | 49 | 14 | 5 |
| A06 | 11.49 | 26.946 | 36.272 | 0.490 | 29 | 11 | 5 |
| A27 | 8.790 | 42.6 | 47.85 | 1.02 | 16 | 64 | 5 |
| I06 | 7.910 | 46.177 | 59.503 | 2.434 | 10 | 45 | 5 |
| I07 | 6.900 | 65.823 | 89.957 | 1.217 | 7 | 40 | 5 |
| H12 | 8.170 | 38.139 | 41.812 | 1.286 | 3 | 33 | 5 |
| H02 | 4.140 | 30.930 | 38.095 | 1.499 | 2 | 45 | 5 |
| I08 | 8.080 | 73.944 | 83.167 | 2.270 | 2 | 38 | 5 |
| A01 | 10.84 | 16.497 | 19.807 | 1.62 | 30 | 23 | 4 |
| G02 | 9.180 | 61.877 | 81.064 | 2.153 | 1 | 10 | 4 |
| H20 | 24.330 | 20.972 | 23.192 | 0.894 | 0 | 23 | 4 |
| I17 | 9.980 | 24.096 | 25.998 | 0.984 | 16 | 44 | 3 |
| C19 | 19.18 | 31.773 | 37.073 | 0.819 | 0 | 27 | 2 |
| I01 | 5.690 | 28.832 | 35.106 | 0.600 | 192 | 15 | 1 |
| I59 | 8.500 | 27.793 | 31.097 | 0.840 | 157 | 8 | 1 |
| J09 | 8.030 | 29.584 | 35.334 | 0.545 | 29 | 17 | 1 |

As shown in Table 8, discordant results were observed in 19 subjects, 13 (68.4%) of which showed discrepancies between the results obtained with the biopsy test compared to the three 4-GX tests. This discrepancy was not unexpected, although it was limited to 6.3% of the total of 205 subjects analysed in this study. Although the direct evaluation of lactase activity in a biopsy of the small intestine is generally considered to be the most accurate of the tests available for the diagnosis of hypolactasia, it has many drawbacks as previously mentioned; apart from being an invasive test, it only indicates the enzyme activity in a specific part or area of the intestine. This part does not generally coincide with that of the highest occurrence of this enzyme (middle jejunum) as it is very difficult to take samples in this area. The results obtained by this test are also very variable between samplings. All of these factors lead to questioning the measurement of lactase activity in duodenal biopsies as the "gold standard" for the diagnosis of hypolactasia. In this sense, the determination of the lactase activity by measurement of the concentration of xylose excreted in the urine or present in the blood following ingestion of 4-GX was demonstrated to reliably reflect the total activity of this enzyme in the small intestine.

The systematic comparison in all patients of this study of the data for lactase in biopsy with the three 4-GX tests, together with the hydrogen breath test and the capillary-blood glucose test enabled us to identify biopsy lactase values in some patients that were clearly discordant with at least 4 of the 5 other tests, the indicate that these lactase measurements in biopsy may reasonably be considered to be false positives or false negatives, again casting doubt on the use of this test for the diagnosis of hypolactasia. As shown in Table 8, the discordance of the biopsy result with at least 4 of the other tests only occurred in one patient (A01), whereas the other results were discordant with the other 5 tests.

After assigning the above value of false positives considered for each of the patients included in Table 9 to the data obtained by the biopsy method, the statistical parameters were recalculated for all of the tests, this time including the data obtained by biopsy, and new ROC curves were obtained making the comparison of the 4-GX tests with the hydrogen breath test and also with the capillary glucose test.

TABLE 9

Results obtained in patients that showed a discrepancy between the values of lactase measured in biopsy and those obtained by the other tests performed.

| Normal limits | ≥ 10 U/g prot | | ≥ 27.58 mg | ≥ 37.87 mg | ≥ 0.97 mg/dL | ≤ 20 ppm | ≥ 25 mg/dL | |
|---|---|---|---|---|---|---|---|---|
| Patient | Biopsy (Ug/prot.) | | 4-GX 4-hour urine (mg) | 4-GX 5-hour urine (mg) | 4-GX blood (mg/dL) | H$_2$ breath test (ppm) | Glycemia (mg/dL) | Diff. |
| A03 | 10.12 | F− | 23.86 | 29.57 | 0.48 | 69 | 0 | 5 |
| I58 | 12.47 | F− | 26.91 | 35.77 | 0.29 | 62 | 14 | 5 |
| I55 | 17.26 | F− | 27.55 | 34.40 | 0.25 | 55 | 11 | 5 |
| C12 | 12.15 | F− | 21.97 | 30.49 | 0.75 | 49 | 14 | 5 |
| A06 | 11.49 | F− | 26.94 | 36.27 | 0.49 | 29 | 11 | 5 |
| A27 | 8.79 | F+ | 42.45 | 47.85 | 1.02 | 16 | 64 | 5 |
| I06 | 7.91 | F+ | 46.17 | 59.50 | 2.43 | 10 | 45 | 5 |
| I07 | 6.90 | F+ | 65.82 | 89.95 | 1.21 | 7 | 40 | 5 |
| H12 | 8.17 | F+ | 38.13 | 41.81 | 1.28 | 3 | 33 | 5 |
| H02 | 4.14 | F+ | 30.83 | 38.09 | 1.49 | 2 | 45 | 5 |
| I08 | 8.08 | F+ | 73.94 | 83.16 | 2.27 | 2 | 38 | 5 |

F−: False negative
F+: False positive

Thus, as shown in Table 9, 11 patients were identified who showed discrepancies in the five diagnostic tests (4-GX and 4-hour and 5-hour urine, 4-GX and blood tests, hydrogen breath test and capillary-blood glucose test) compared to the biopsy test (5.4% of the total of 205 subjects analysed in this study). Consequently, the results for subjects A03, A06, C12, 155 and 158 were considered as false negatives for the biopsy test and true positives for the other tests, while subjects A27, H02, H12, 106, 107, and 108 were considered as false positives for the biopsy test and true negatives for the other tests. After correcting the diagnosis obtained from the biopsy test as indicated in Table 9, the reliability parameters of the six tests used in this study for the evaluation of hypolactasia were recalculated in accordance with the final criteria established in Table 9, applying the final criterion of false negative (F−) or false positive (F+) in the biopsy as established by the concordance with the 5 other tests. Consequently, the final number of concordant results in all six diagnostic tests and the criteria for this diagnostic were 102 (95.3%), 103 (96.3%), 106 (99.1%), 104 (97.2%), 84 (78.5%) and 80 (74.8%) for the positive results of lactase activity in biopsy, 4-GX and 4-hour urine test, 4-GX and 5-hour urine test, 4-GX and blood test, hydrogen breath test and capillary-blood glucose test respectively.

The number of negative results in all the tests were 92 (93.9%), 96 (98.0%), 95 (96.9%), 95 (96.9%), 89 (90.8%), and 82 (83.7%), respectively. Similarly, new ROC curves were obtained making the comparison of the 4-GX tests with the hydrogen breath test and the capillary-blood glucose test.

Figure 3:
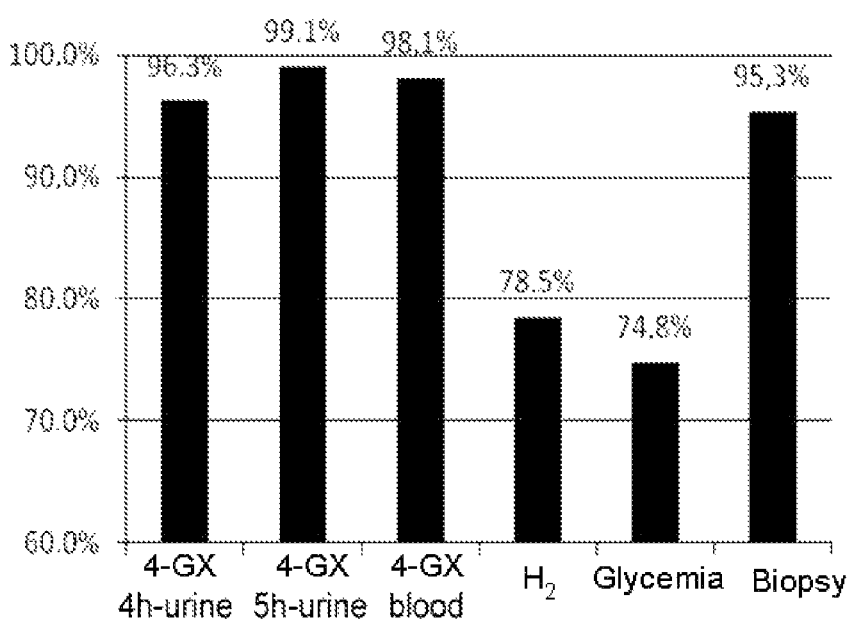
FIG. 3. Percentages of sensitivity (A), specificity (B), positive predictive value (C), negative predictive value (D), positive likelihood ratio (E) and negative likelihood ratio (F) of the various tests performed in patients (n=205) with symptoms suggestive of lactose intolerance after the administration of various doses of 4-GX compared to the determination of intestinal lactase activity in biopsy taken as the gold standard test after recalculating the statistical parameters taking into account the false positive values for the patients included in Table 9.
Figure 3:
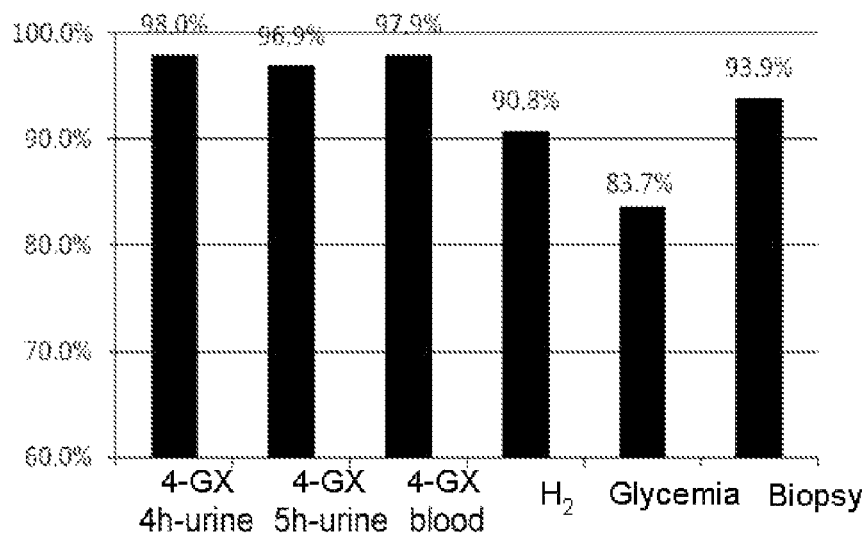
Figure 3:
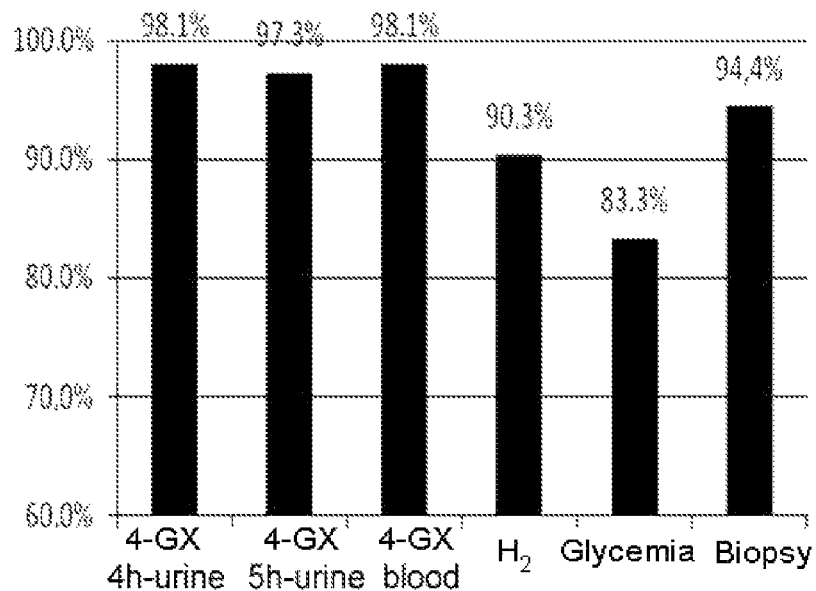
Figure 3:
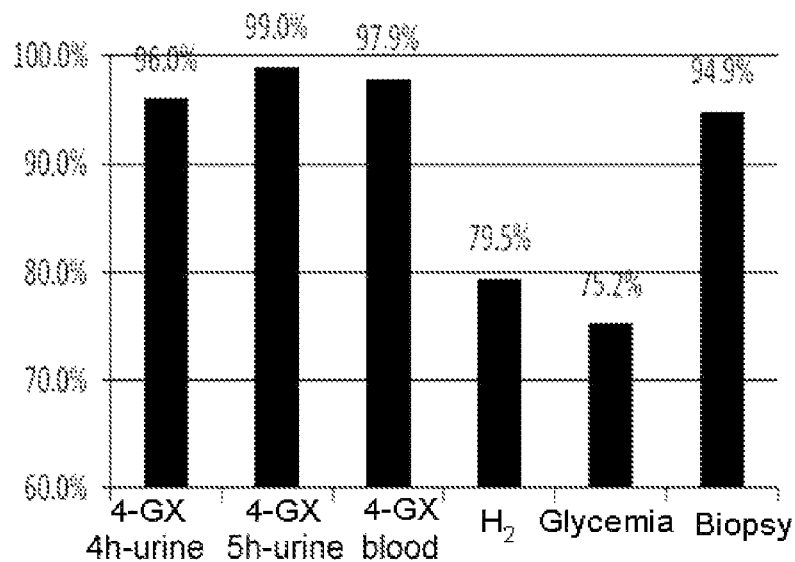

As shown in Table 10 and in FIG. 3, after correcting the results of diagnosis by biopsy, the recalculated values for sensitivity, specificity, positive and negative predictive values for all of the diagnostic tests of intestinal lactase deficiency by the administration of 4-GX were above 95%, varying between the ranges of 96.00-98.10 for the 4-hour urine test, 96.94-99.07 for the 5-hour urine test and 97.94-98.11 for the blood test. These values were far higher than for any of the other diagnostic tests used in this study, including the values obtained by the biopsy test. The values obtained for the statistical parameters of sensitivity, specificity, positive predictive values and negative predictive values were much better than those obtained with the hydrogen breath test and those obtained with the capillary-blood glucose test (see Table 10 and FIG. 3). In this sense, the percentages of false negatives for the 4-GX and 4-hour urine test, 5-hour urine test and blood test were 3.74%, 0.93% and 1.89%, respectively (with a sensitivity of 96.26%, 99.07% and 98.11%, respectively), compared to the percentages of false negatives of 4.67% (sensitivity of 95.33%), 21.50% (sensitivity of 78.50%), and 25.23% (sensitivity of 74.77%) obtained for the biopsy test, hydrogen breath test and capillary-blood glucose test respectively. The positive likelihood ratios for the 4-GX tests (FIG. 3E) were 2 to 3 times higher than for the biopsy test (47.168, 32.361, and 47.585 for the 4-GX and 4-hour and 5-hour urine and blood tests respectively compared to 15.570 for the biopsy test), and 4 to 5 times higher than the hydrogen breath test (8.548), and 7 to 10 times higher than the capillary-blood glucose test (4.579). Lastly, the negative likelihood ratios (FIG. 3F) for the 4-GX tests were 1.3 to 5 times less than those obtained for the biopsy test (0.038, 0.010, and 0.019 for the 4-GX and 4-hour and 5-hour urine and blood tests respectively compared to 0.050 for the biopsy test), 6 to 20 times less than those obtained for the hydrogen breath test (0.237), and 8 to 30 times less than those in the capillary-blood glucose test (0.302).

TABLE 10

Statistical parameters obtained after correction of the biopsy diagnostic result (five discrepancies in the tests described in the invention compared to the biopsy test).

| | | CI 95% |
|---|---|---|
| 4-GX test in 4-hour urine | | |
| Sensitivity (%) | 96.26 | 90.70 to 98.97 |
| Specificity (%) | 97.96 | 92.82 to 99.75 |
| Positive predictive value (%) | 98.10 | 93.29 to 99.77 |
| Negative predictive value (%) | 96.00 | 90.07 to 98.90 |
| 4-GX test in 5-hour urine | | |
| Sensitivity (%) | 99.07 | 94.90 to 99.98 |
| Specificity (%) | 96.94 | 91.31 to 99.36 |
| Positive predictive value (%) | 97.25 | 92.17 to 99.43 |
| Negative predictive value (%) | 98.96 | 94.33 to 99.97 |

TABLE 10-continued

Statistical parameters obtained after correction of the biopsy diagnostic result (five discrepancies in the tests described in the invention compared to the biopsy test).

|  |  | CI 95% |
|---|---|---|
| 4-GX blood test | | |
| Sensitivity (%) | 98.11 | 93.35 to 99.77 |
| Specificity (%) | 97.94 | 92.75 to 99.75 |
| Positive predictive value (%) | 98.11 | 93.35 to 99.77 |
| Negative predictive value (%) | 97.94 | 92.75 to 99.75 |
| Hydrogen breath test | | |
| Sensitivity (%) | 78.50 | 69.51 to 85.86 |
| Specificity (%) | 90.82 | 83.28 to 95.71 |
| Positive predictive value (%) | 90.32 | 82.42 to 95.48 |
| Negative predictive value (%) | 79.46 | 70.80 to 86.51 |
| Capillary-blood glucose test | | |
| Sensitivity (%) | 74.77 | 65.45 to 82.67 |
| Specificity (%) | 83.67 | 74.84 to 90.37 |
| Positive predictive value (%) | 83.33 | 74.35 to 90.16 |
| Negative predictive value (%) | 75.23 | 66.04 to 83.00 |
| Biopsy test | | |
| Sensitivity (%) | 95.33 | 89.43 to 98.47 |
| Specificity (%) | 93.88 | 87.15 to 97.72 |
| Positive predictive value (%) | 94.44 | 88.30 to 97.93 |
| Negative predictive value (%) | 94.85 | 88.38 to 98.31 |

CI: confidence interval.

Figure 4:
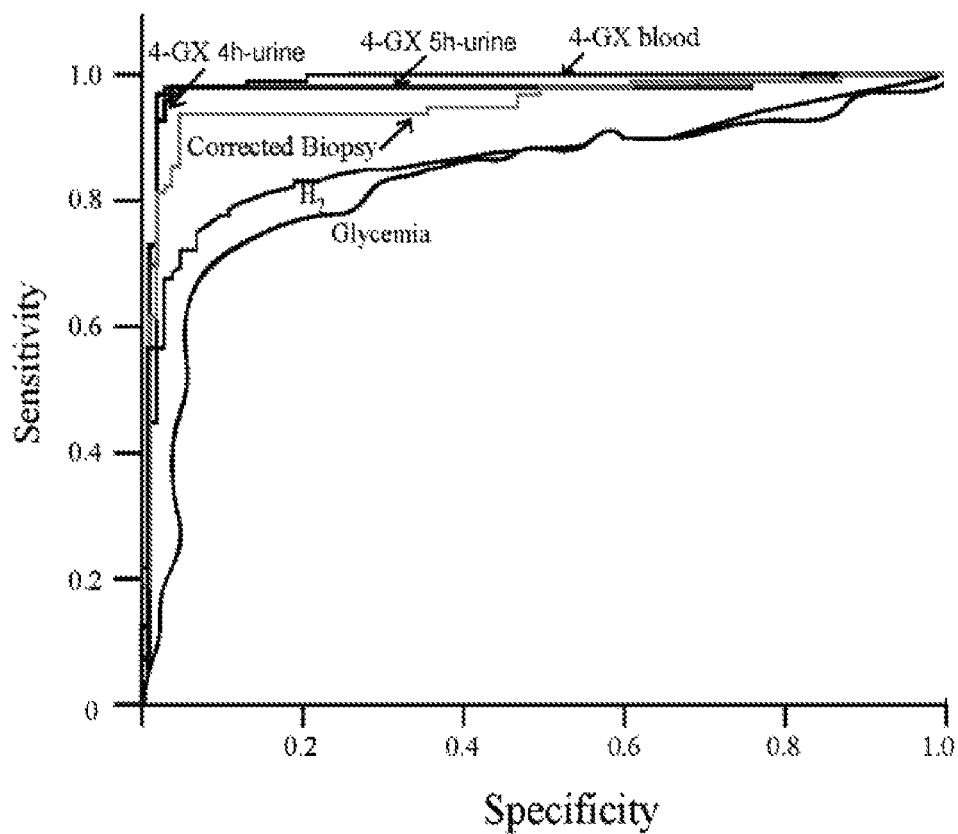
FIG. 4. ROC curves of the various tests performed on patients with symptoms suggestive of lactose intolerance after the administration of various doses of 4-GX compared to the determination of intestinal lactase activity in biopsy taken as the gold standard test after recalculating the statistical parameters taking into account the false positive values and false negative values for the patients included in Table 9.

FIG. 4 shows the new ROC curves of the 4-GX and 4-hour urine, 5-hour urine and blood tests respectively compared to the other tests used in the study, the hydrogen breath test, capillary-blood glucose test and biopsy test after correcting the diagnosis of the results obtained from the biopsy test. The three curves corresponding to the results obtained with the three 4-GX tests are displaced far to the upper left corner, compared to the other ROC curves for the other diagnostic tests including biopsy. FIG. 4 shows that the areas under the ROC curves for the 4-GX tests are now close to the ideal value of 1.0 (varying from 0.9758 to 0.9894), these values being higher than those obtained for the hydrogen breath test (0.8852, $p<0.0001$ to 0.0008), capillary-blood glucose test (0.8512, $p<0.0001$) and biopsy test (0.9613 but in this case the p value was not significant with p varying from 0.08 to 0.5110).

As previously mentioned, one of the patients enrolled in the present trial (A01) presented discordance between the values obtained by the biopsy test compared to at least four of the tests described in the present invention. This patient was a false negative. Taking this data point into account, the statistical parameters of all the tests were recalculated, corrected by the biopsy diagnostic result and showing discrepancies in at least four of the tests performed compared to the biopsy test (Table 11). The statistical parameters obtained are very similar to those shown in Table 10, where the statistical parameters of all the tests, corrected by the biopsy diagnostic result and showing discrepancies in five of the tests performed compared to the biopsy test. Nevertheless, the global conclusions on the reliability parameters of the tests for intestinal lactase activity, either the urine and/or blood tests, by the administration of 4-GX described in the invention were unchanged, after taking into account the discrepancies of the results obtained from these tests compared to the discrepancies of the results obtained with at least four or five of the other tests used.

TABLE 11

Statistical parameters obtained after correction of the biopsy diagnostic result (four discrepancies in the tests described in the invention compared to the biopsy test).

|  |  | CI 95% |
|---|---|---|
| 4-GX test in 4-hour urine | | |
| Sensitivity (%) | 97.20 | 92.02 to 99.42 |
| Specificity (%) | 98.98 | 94.45 to 99.97 |
| Positive predictive value (%) | 99.05 | 94.81 to 99.98 |
| Negative predictive value (%) | 97.00 | 91.48 to 99.38 |
| 4-GX test in 5-hour urine | | |
| Sensitivity (%) | 100.00 | 96.61 to 100.00 |
| Specificity (%) | 97.96 | 92.82 to 99.75 |
| Positive predictive value (%) | 98.17 | 93.53 to 99.78 |
| Negative predictive value (%) | 100.00 | 96.23 to 100.00 |
| 4-GX blood test | | |
| Sensitivity (%) | 99.06 | 94.86 to 99.98 |
| Specificity (%) | 98.97 | 94.39 to 99.97 |
| Positive predictive value (%) | 99.06 | 94.86 to 99.98 |
| Negative predictive value (%) | 98.97 | 94.39 to 99.97 |
| Hydrogen breath test | | |
| Sensitivity (%) | 78.50 | 69.51 to 85.86 |
| Specificity (%) | 90.82 | 83.28 to 95.71 |
| Positive predictive value (%) | 90.32 | 82.42 to 95.48 |
| Negative predictive value (%) | 79.46 | 70.80 to 86.51 |
| Capillary-blood glucose test | | |
| Sensitivity (%) | 74.77 | 65.45 to 82.67 |
| Specificity (%) | 83.67 | 74.84 to 90.37 |
| Positive predictive value (%) | 83.33 | 74.35 to 90.16 |
| Negative predictive value (%) | 75.23 | 66.04 to 83.00 |
| Biopsy test | | |
| Sensitivity (%) | 94.39 | 88.19 to 97.91 |
| Specificity (%) | 92.86 | 85.84 to 97.08 |
| Positive predictive value (%) | 93.52 | 87.10 to 97.35 |
| Negative predictive value (%) | 93.81 | 87.02 to 97.70 |

CI: confidence interval.

As demonstrated by the data shown in the present invention, the accuracy of the 4-GX and 4-hour and 5-hour urine, and blood tests at doses of 0.5 g and 3 g (or 0.45 g and 2.7 g, respectively, in a 4-GX sample including 10 wt % water) respectively for the diagnosis of hypolactasia, taking into account the normal limits described in the present invention and quantified by the sensitivity, specificity, positive predictor value and negative predictor value parameters as well as the area under the ROC curves, was significantly better than that shown by the hydrogen breath test or the capillary-blood glucose test following an overload of lactose.

The reliability of the 4-GX tests was also shown to be better than the measurement of lactase activity in a sample of intestinal mucosa extracted by biopsy, there not being any other functional test for the diagnosis of hypolactasia with similar reliability, so these new tests have the potential of becoming the gold standard tests for the diagnosis of this disorder. This characteristic together with their being non-invasive tests, the absence of reactions in intolerant patients and the simplicity of conducting the tests makes these new tests into the optimum functional diagnostic tool for the diagnosis of lactose intolerance.

The three tests with 4-GX and 4-hour urine, 5-hour urine and blood have very similar reliability characteristics, so clinical practice can select any of them depending on the clinical features of the patient. In this sense, perhaps the 4-GX test and 5-hour urine shows the highest sensitivity, despite having a slightly lower specificity, so this might be the advantage of this test because the risk of a false negative diagnosis may be higher than the risk of a false positive diagnosis. Also, the 4-GX and 5-hour urine test offers better measurement of the total amount of excreted xylose in the case, for example, of patients with a delay in gastric emptying. On the other hand, the 4-GX and blood test provides an alternative to the urine test, especially in small children and infants where urine collection can be problematic, and it also requires a shorter fasting time. A combination of both tests, 4-GX and 5-hour urine and 90-minute blood tests would improve the accuracy of xylose determination in some patients, for example patients with renal dysfunction, that can give incorrectly low values for urinary xylose.

In the prior art, none of the parameters of the amount of 4-GX to be administered in the test, the time to wait before evaluating intestinal lactase activity applied specifically to each test biological fluid: urine or blood (plasma), had been determined in such a way as to enable distinguishing false positives in such a statistically effective way, that would make the test into a gold standard or reference test for the diagnosis of this disease, better than the other invasive or non-invasive tests described in the state of the art. The 4-GX and urine or blood test is a safe and innocuous method for the non-invasive diagnosis of hypolactasia with a virtual absence of the most common inherent abdominal discomforts associated with the use of the hydrogen breath test and the capillary-blood glucose test when performed in lactose-intolerant subjects. The 4-GX test is simple and only requires the determination of xylose excreted in urine or present in blood, which are routine determinations in clinical laboratories. The excellent results shown in the present invention and obtained by the use of the 4-GX and urine and/or blood tests substantially improve the diagnosis of hypolactasia compared to the methods currently used, including the measurement of lactase activity in small intestinal biopsy samples, so that the test of the invention could be proposed as a new gold standard test in the diagnostic study of lactose intolerance. Furthermore, using the test described in the present invention, it was also possible to correctly diagnose and differentiate between individuals with lactose intolerance due to allergies and those with enzyme deficiencies of intestinal lactase.

REFERENCES

Arola, H. (1994) Diagnosis of hypolactasia and lactose malabsorption. Scand. J. Gastroenterol. 202 (29 Suppl), 22-35.
Davidson, G. P., & Robb, T. A. (1985) Value of breath hydrogen analysis in management of diarrheal illness in childhood: Comparison with duodenal biopsy. J. Pediatr. Gastroenterol. Nutr. 4, 381-387.
Dawson, D. J., Lobley, R. W., Burrows, P. C., Miller, V. & Holmes, R. (1986) Lactose digestion by human jejunal biopsies: the relationship between hydrolysis and absorption. Gut 27, 521-527.
ES478590. Procedimiento de obtención de 3-metil-lactosa utilizable para la evaluación de la lactasa intestinal.
ES482073. Mejoras en la patente principal por procedimiento de obtención de 3-metil-lactosa utilizable para la evaluación de la lactosa intestinal.
ES2023556. Procedimiento de obtención de 4-O-Beta-D-galactopiranosil-D-xilosa utilizable para la evaluación diagnóstica de la lactasa intestinal.
ES2100131. Procedimiento enzimático de obtención de β-D-galactopiranosil-D-xilosas utilizables para la evaluación diagnóstica de la lactasa intestinal.
ES2182703. Un procedimiento enzimático para obtener 4-O-β-D-galactopiranosil-D-xilosa, 4-O-β-D-galactopiranosil-D-xilosa obtenida de acuerdo con el procedimiento, composiciones que la contienen y su use en la evaluación de la lactasa intestinal.
ES2208099. Empleo de 4-galactosil-xilosa en humanos para la evaluación in vivo de lactasa intestinal como prueba diagnóstica no invasiva de la deficiencia de este enzima.
Koetse, H. A., Stellaard, F., Bijleveld, C. M., Elzinga, H., Boverhof, R., Van der Meer, R., Vonk, R. J. & Sauer, P. J. (1999) Non-invasive detection of low intestinal lactase activity in children by use of a combined $^{13}CO_2/H_2$ breath Test. Scand. J. Gastroenterol. 34, 35-40.
Levitt, M. D. (1969) Production and excretion of hydrogen gas in man. N. Engl. J. Med. 281, 122-127.
Lifshitz, C. H. Bautista, A., Gapalachrishna, G. S., Stuff, J. & Garza, C. (1985) Absorption and tolerance of lactose in infants recovering from severe diarrhea. J. Pediatr. Gastroenterol. Nutr. 4, 942-94845,46.
McGill, D. B. & Newcomer, A. D. (1967) Comparison of venous and capillary blood samples in lactose tolerance testing. Gastroenterology 53, 371-374.
Metz, G., Jenkins, D. J., Peters, T. J., Newman, A. & Blendis, L. M. (1975) Breath hydrogen as a diagnostic method for hypolactasia. Lancet 1, 1155-1157.
Newcomer, A. D. & McGill, D. B. (1966) Distribution of disaccharidase activity in the small bowel of normal and lactase-deficient subjects. Gastroenterology 51, 481-488.
Newcomer, A. D., McGill, D. B., Thomas, P. J. & Hofmann, A. F. (1975) Prospective comparison of indirect methods for detecting lactase deficiency. N. Engl. J. Med. 293, 1232-1236.
Newcomer, A. D., McGill, D. B., Thomas, P. J. & Hofmann, A. F. (1975) Prospective comparison of indirect methods for detecting lactase deficiency. N. Engl. J. Med. 293, 1232-1236.
Scriber, C. R., Beaudet, A. L., Sly, W. S., Valle, D., Childs, B., Kinzler, K. W. and Vogelstein, B. Eds Vol I, pp 1623-1650. McGraw-Hill, New York.
Scriber, C. R., Beaudet, A. L., Sly, W. S., Sasaki, Y., Lio, M., Kameda, H,. Ueda, H. & Aoyagi, T. (1970) Measurement of $^{14}C$-lactose absorption in the diagnosis of lactase deficiency. J. Lab. Clin. Med. 76, 824-835.
Semenza, G. et al. 2001. The Metabolic and Molecular Bases of Inherited Disease. McGraw-Hill. Vol I, pp 1623-1650.
Triadou, N., Bataille, J. & Schmitz, J. (1983) Longitudinal study of the human intestinal brush border membrane proteins distribution of the main disaccharidases and peptidases. Gastroenterology 85, 1326-1332.
Valle, D., Childs, B., Kinzler, K. W. and Vogelstein, B. Eds) Vol I, pp 1623-1650. McGraw-Hill, New York.

The invention claimed is:
1. Non-invasive diagnostic method for evaluation of intestinal lactase deficiency that comprises the stages of:
a) Extracting a blood sample from the individual who is the object of the test after fasting for 8 hours;
b) Administering via the oral route to the individual who is the object of the test a quantity of 4-O-β-D-galactopyranosyl-D-xylose (4-GX) of between 0.125 g and 6 g;
c) Extracting a blood sample from this individual at 90 minutes following the administration of 4-GX;

d) Determining in vitro the concentration of xylose in the blood sample extracted in step a);

e) Determining in vitro the concentration of xylose in the blood sample extracted in step c);

f) Subtracting the values of xylose concentrations obtained in vitro in step e) from those obtained in vitro in step (d);

g) Comparing the value obtained in step f) with a reference threshold value obtained in vitro from a population of healthy control individuals subjected to the same protocol, below which threshold the subject is considered to be suffering from intestinal lactase deficiency (hypolactasia), wherein the reference threshold value of the blood xylose concentration is 0.41 mg/dL, 0.53 mg/dL, 0.97 mg/dL, and 1.44 mg/dL when the initial quantity of 4-GX is 0.5 g, 1 g, 3 g, and 6 g, respectively.

2. The method according to claim 1, wherein the determination of the blood xylose concentration is performed using plasma.

3. The method according to claim 1, wherein the doses of 4-GX administered are selected from: 0.5 g, 1 g, 3 g and 6 g.

4. The method according to claim 3, wherein the dose of 4-GX to be administered is 3 g.

5. The method according to claim 1, wherein the reference threshold value of the blood xylose concentration following administration to the patient of the dose of 0.5 g of 4-GX is 0.41 mg/dL.

6. The method according to claim 1, wherein the reference threshold value of the blood xylose concentration following administration to the patient of the dose of 1 g of 4-GX is 0.53 mg/dL.

7. The method according to claim 1, wherein the reference threshold value of the blood xylose concentration following administration to the patient of the dose of 3 g of 4-GX is 0.97 mg/dL.

8. The method according to claim 1, wherein the reference threshold value of the blood xylose concentration following administration to the patient of the dose of 6 g of 4-GX is 1.44 mg/dL.

* * * * *